United States Patent [19]

Zahler et al.

[11] Patent Number: 5,059,690

[45] Date of Patent: Oct. 22, 1991

[54] PURINYL TETRAHYDROFURANS

[75] Inventors: Robert Zahler, Princeton; Joseph A. Tino, Robbinsville, both of N.J.

[73] Assignee: E. R. Squibb & Sons, Inc., Princeton, N.J.

[21] Appl. No.: 486,988

[22] Filed: May 1, 1990

[51] Int. Cl.$^5$ .............. A61K 31/52; C07D 473/18; C07D 473/30; C07D 473/34

[52] U.S. Cl. .............. 544/276; 544/244; 544/265; 544/277; 544/313; 544/314; 544/317; 544/243; 549/476

[58] Field of Search .............. 544/276, 277, 265, 244; 514/266, 262; 536/55

[56] References Cited

U.S. PATENT DOCUMENTS

| 4,788,181 | 11/1988 | Driscoll et al. | 514/49 |
| 4,855,466 | 8/1989 | Zahler et al. | 549/546 |
| 4,918,075 | 4/1990 | Zahler et al. | 514/262 |

FOREIGN PATENT DOCUMENTS

| 285884 | 10/1988 | European Pat. Off. |
| 335355 | 10/1989 | European Pat. Off. |
| 391411 | 10/1989 | European Pat. Off. |
| 57-14679 | 9/1982 | Japan |
| 88/07532 | 10/1988 | PCT Int'l Appl. |
| 2021582 | 12/1979 | United Kingdom |

OTHER PUBLICATIONS

Ueda et al., "Chemical Conversion of Nucleosides...", Nucleic Acids Research, Symposium #9, 1981, pp. 91–94.
Shuto et al., "Chemical Conversion of Uridine to...", Nucleosides & Nucleotides, 1(3), 263–273 (1982).
Rosenthal et al., "Branched-Chain Sugar Nucleosides...", Canadian Jour. of Chem., vol. 47, pp. 4477–4481 (1969).
Acton et al., "Improved Antitumor Effects...", Jour. Med. Chem., vol. 22, pp. 518–525 (1979).
Bamford et al., "Synthesis and Antiviral Activity...", Jour. Med. Chem., vol. 33, pp. 2494–2501 (1990).
Pudlo et al., "A New Novel Approach Towards...", Tetrahedron Letters, vol. 31, pp. 3101–3104 (1990).
Slusarchyk et al., U.S. Serial No. 322,375 filed 3/13/89.
DeClercq et al., "Targets for the Design of Antiviral Agents", 1983, pp. 203–230.
Herdewijn et al., "Synthesis and Antiviral Activity...", J. Med. Chem., 1985, vol. 28, pp. 550–555.
Takano et al., "Enantio-Controlled Route...", J. Chem. Soc. Chem. Commun., 1988, pp. 189–191.

Primary Examiner—Diana G. Rivers
Attorney, Agent, or Firm—Stephen B. Davis

[57] ABSTRACT

Antiviral activity is exhibited by compounds having the formula

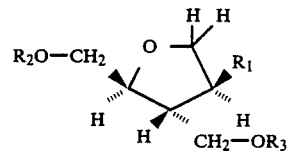

and pharmaceutically acceptable salts thereof wherein $R_1$ is a purine or pyrimidine base or an analog thereof and $R_2$ and $R_3$ are independently hydrogen, $-PO_3H_2$ or

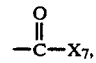

wherein $X_7$ is hydrogen, alkyl, substituted alkyl or aryl.

13 Claims, No Drawings

PURINYL TETRAHYDROFURANS

BRIEF DESCRIPTION OF THE INVENTION

This application is a continuation-in-part of co-pending application Ser. No. 342,048 filed Apr. 24, 1989 now abandoned.

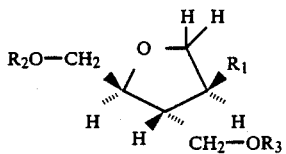

and pharmaceutically acceptable salts thereof. In formula 1, and throughout the specification, the symbols are as defined below.

$R_1$ is

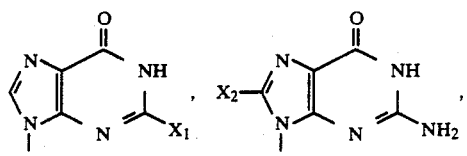

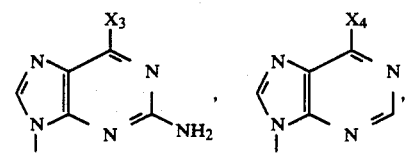

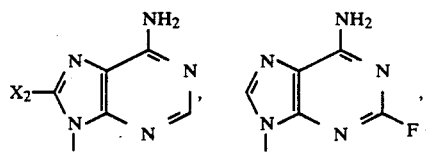

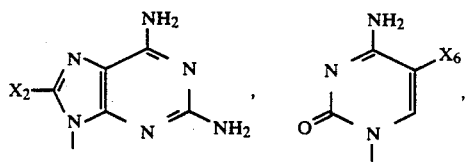

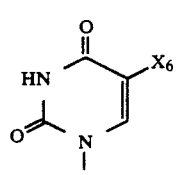

wherein $X_1$ is hydrogen, amino,

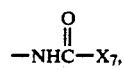

and —N=CHN$(X_8)_2$ $X_2$ is methyl, fluoro, chloro, bromo, iodo, hydroxy, or amino, $X_3$ is hydrogen, chloro, or O—$X_8$, $X_4$ is amino, chloro,

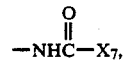

or —N=CHN$(X_8)_2$, bromon, iodo, hydroxy, or amino, $X_6$ is fluoro, chloro, bromo, iodo, hydrogen, methyl, trifluoromethyl, ethyl, n-propyl, 2-fluoro-ethyl, 2-chloroethyl, or

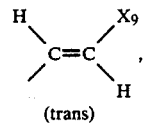

(trans)

$X_7$ is hydrogen, alkyl, substituted alkyl, or aryl, $X_8$ is alkyl, $X_9$ is chloro, bromo, iodo, hydrogen, methyl, or trifluoromethyl, $R_2$ and $R_3$ are independently hydrogen, —PO$_3$H$_2$, or

Referred compounds of formula 1 are when $R_1$ is

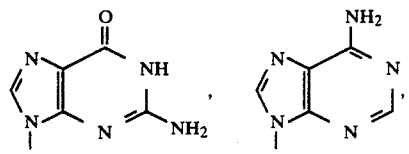

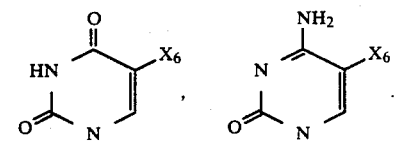

Most preferred compounds of formula 1 are when $R_1$ is

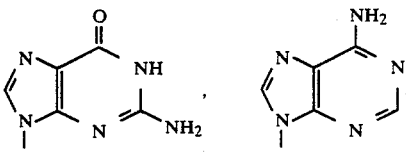

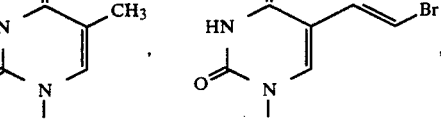

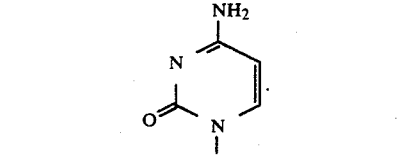

The term "alkyl" refers to both straight and branched chain groups. Those groups having 1 to 10 carbons are preferred. The term "substituted alkyl" refers to alkyl groups having one or more substituents. Preferred substituents are halogen, amino, azido, hydroxy, cyano, trialkylammonium (wherein each alkyl group has 1 to 6 carbons), alkoxy of 1 to 6 carbons, aryl and carboxy. The term "aryl" refers to phenyl and phenyl substituted with one, two or three substituents. Preferred substituents are alkyl of 1 to 6 carbons, alkoxy of 1 to 6 carbons, halogen, trifluoromethyl, amino, alkylamino, dialkylamino, nitro, cyano, alkanoyloxy of 2 to 11 carbons, carboxy, carbamoyl and hydroxy.

DETAILED DESCRIPTION OF THE INVENTION

The compounds of formula 1, and the pharmaceutically acceptable salts thereof, are antiviral agents that can be used to treat viral infection in mammalian species such as domesticated animals (e.g., dogs, cats, horses and the like) and humans, and avian species (e.g., chickens and turkeys).

The compounds of formula 1 wherein $R_1$ is

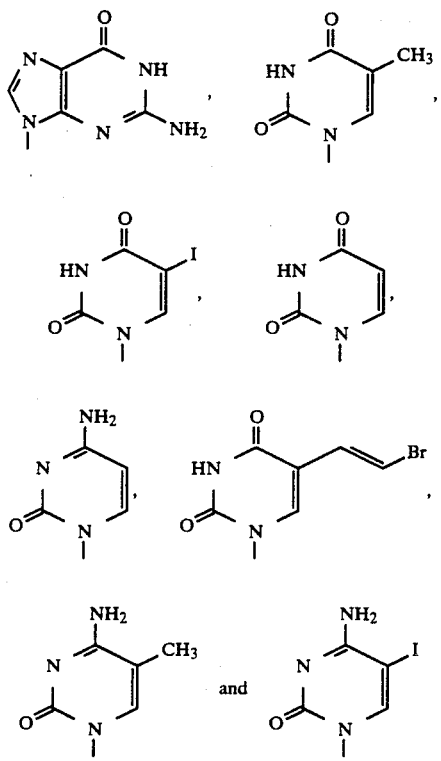

are effective against one or more of the following viruses: herpes simplex virus 1 and 2, varicellazoster virus, cytomegalovirus, and vaccinia virus. They are also believed to be active against a variety of other DNA viruses. Exemplary DNA viruses in addition to those named above include other herpes viruses (e.g., Epstein-Barr virus, pseudorabies virus, human herpes virus 6 and the like), other poxviruses (e.g., monkey pox and myoma), papovaviruses (e.g., the papilloma viruses), hepatitis B virus, and adenoviruses.

The compounds of formula 1 wherein $R_1$ is

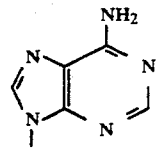

are effective against one or more of the following viruses: herpes simplex 1 and 2, varicella-zoster virus, cytomegalovirus, and vaccinia virus. They are also active against human immunodeficiency virus (HIV), other retroviruses, and other DNA viruses. Exemplary DNA viruses in addition to those named above include other herpes viruses (e.g., Epstein-Barr virus, pseudorabies virus human herpes virus 6 and the like) other poxviruses (e.g. monkey pox and myoma), papovaviruses (e.g. the papilloma viruses) hepatitis B virus, and adenoviruses. Exemplary retroviruses other than that named above are those affecting man, such as human T-cell lymphotropic viruses I and II, and those affecting other animals, such as feline leukemia virus, murine leukemia virus, and equine infectious anemia virus.

All of the other compounds of formula 1 are believed to be active against one or more of the following viruses: herpes simplex virus 1 and 2, varicella-zoster virus, cytomegalovirus, vaccinia virus and the retroviruses and other DNA viruses described above.

The compounds of this invention may be administered parenterally (for example, by intravenous, intraperitoneal, or intramuscular injection), orally, or topically.

The compounds may be administered orally or parenterally in an amount effective to treat the infection. The dosage will, of course, depend on the severity of the infection, but will likely be in the range of about 1.0 to 50 mg/kg of body weight. The desired dose may be administered several times daily at appropriate intervals.

For infections of the eye, or other external tissues, (e.g., mouth and skin) the compositions may be applied to the infected part of the body of the patient topically as an ointment, cream, aerosol, gel, powder, lotion, suspension or solution (e.g., as eye drops). The concentration of the compound in the vehicle will, or course, depend on the severity of the infection, but will likely be in the range of about 0.1 to 7% by weight.

The compounds of this invention can be prepared from the compound having the formula $$\text{BnO} \overset{O}{\underset{\text{BnO}}{\diagdown}} X_{10} \qquad 2$$

wherein $X_{10}$ is an alkyl or aryl sulfonate, such as p-toluenesulfonyloxy, methanesulfonyloxy, p-nitrophenylsulfonyloxy, or trifluoromethylsulfonyloxy, and "Bn" is $$\text{C}_6\text{H}_5-\text{CH}_2-.$$

Using a modification of literature procedures (see P. A. Levene, et.al., *J. Biol Chem.*, 102, 317, 331 (1933); H. Kuzuhara, et.al., *Agr. Biol. Chem.*, 28, 900 (1964); A. Rosenthal, et. al., *Tetrahedron Lett.*, 397 (1969); A. Rosenthal, et.al., *Carbohydrate Res.*, 16, 337 (1971) the known compound 3 can be prepared from 1,2-O-(1-methylethylidene)-α-D-xyloguranose (compound 4) as outlined in Scheme 1:

Scheme 1

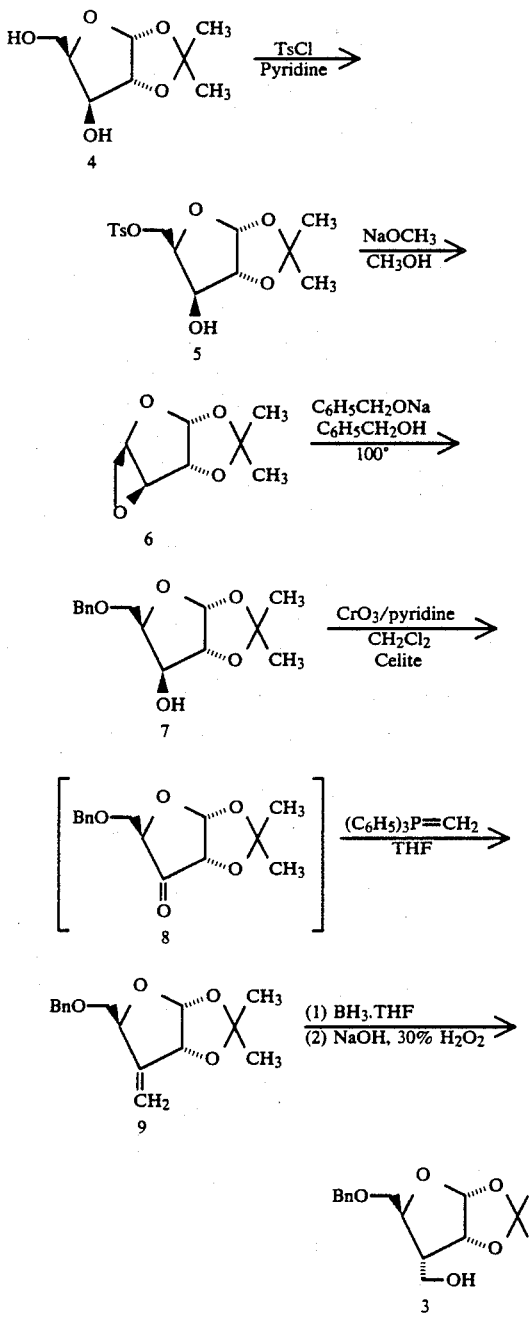

Treatment of compound 4 with α-toluenesulfonyl chloride (TsCl) in pyridine provides compound 5, which, upon exposure to sodium methoxide in methanol gives compound 6. Treatment of compound 6 with the sodium salt of benzyl alcohol yields compound 7. Oxidation of compound 7 with Collin's reagent [chromium(VI) oxide-pyridine] in methylene chloride provides compound 8 which is treated, without purification, with triphenylphosphinemethylene to give compound 9. Reaction with borane-tetrahydrofuran complex, followed by an oxidative workup, provides the known compound 3.

Treatment of compound 3 with sodium hydride/dimethylsulfoxide, followed by benzyl bromide provides the compound of formula

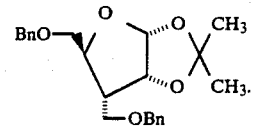

10

Hydrolysis of the ketal of compound 10 with acetic acid/water, followed by acetylation of the resulting diol with acetic anhydride in pyridine, gives the compound of formula

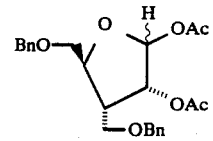

11 as a mixture of epimers.

Reaction of compound 11 with bromotrimethylsilane, followed by reduction with diisobutylaluminum hydride provides the compound of formula

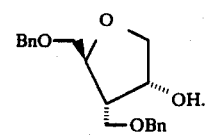

12

Alternatively, reaction of compound 11 with hydrogen chloride followed by reduction with diisobutylaluminum hydride provides the compound of formula 12.

The compound having the formula 2 can be prepared from compound 12 by methods well-known in the art. For example, treatment with α-toluenesulfonyl chloride in pyridine, or methanesulfonyl chloride in pyridine or triethylamine, provides the corresponding compound of formula 2 wherein $X_{10}$ is p-toluenesulfonyloxy or methanesulfonyloxy, respectively.

Treatment of a compound of formula 2 with a compound of formula

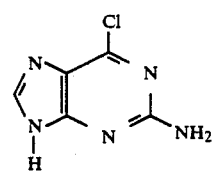

13 in the presence of a base such as potassium carbonate, sodium hydride, or potassium hydride in an aprotic polar solvent such as dimethylformamide, dimethyl sulfoxide, or sulfolane (tetramethylene sulfone) yields the corresponding compound of formula

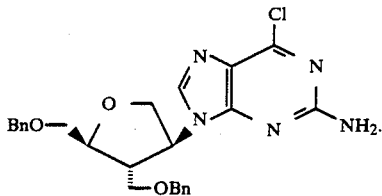

14

Optionally, the reaction can be run in the presence of a metal chelator such as 18-crown-6 (1,4,7,10,13,16-hexaoxacyclooctadecane) or 15-crown-5 (1,4,7,10,13-pentaoxacyclopentadecane).

Removal of the benzyl protecting groups from a compound of formula 14 yields a compound of formula 1 wherein $R_1$ is

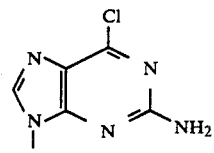

and $R_2$ and $R_3$ are hydrogen. The benzyl protecting groups can be removed by treatment with boron trichloride in dichloromethane.

Reaction of a compound of formula 2 with a compound of formula

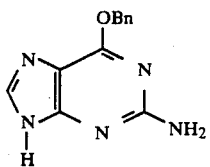

15 under conditions analogous to those used in the preparation of compound 14 provides a compound of formula

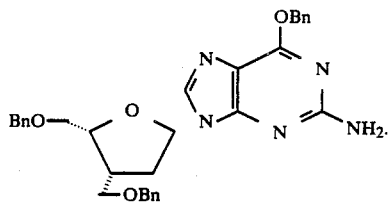

16

Removal of the benzyl protecting groups from a compound of formula 16 yields a compound of formula 1 wherein $R_1$ is

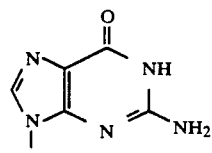

and $R_2$ and $R_3$ are hydrogen.

The three benzyl protecting groups can be removed at the same time by using sodium in liquid ammonia, by hydrogenolysis (e.g. palladium hydroxide on carbon in cyclohexene and ethanol), or by using boron trichloride in dichloromethane. Alternatively, the purine-O-benzyl group can be removed first using aqueous alcoholic mineral acid followed by removal of the remaining two benzyl ethers using, for example, sodium in liquid ammonia or hydrogenolysis.

Alternatively this compound of formula 1 can be prepared from a compound of formula 14. For example, removal of the benzyl groups can be effected first by treatment with boron trichloride, and then the chloro group can be hydrolized using aqueous acid (e.g.,aqueous hydrochloric acid) or base (e.g., sodium hydroxide in aqueous dioxane). Alternatively, the chloro group can be hydrolized first, followed by removal of the benzyl groups.

Alternatively this compound of formula 1 can be prepared by removal of the benzyl protecting groups from a compound of formula 14 followed by treatment with adenosine deaminase by methods known in the art (e.g., M. J. Robins and P. W. Hatfield, Can. J. Chem., 60, 547 (1982)).

A compound of formula 1 wherein $R_1$ is

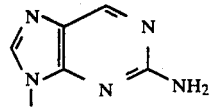

and $R_2$ and $R_3$ are hydrogen can be prepared from a compound of formula 14. For example, deprotection of the benzyl groups and reduction of the chloro group can be accomplished simultaneously by hydrogenation (e.g., ammonium formate and palladium black or palladium on carbon in methanol or ethanol; palladium hydroxide on carbon in cyclohexene and ethanol; or palladium on carbon, hydrogen and ethanol).

Alternatively, this compound of formula 1 can be prepared by reacting an optionally protected compound of formula

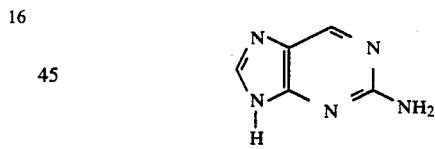

17 with a compound of formula 2 according to the procedures analogous to those used in the preparation of a compound of formula 14, followed by removal of the protecting groups by methods known in the art. The optionally protected forms of compound 17 can be protected at the amino (—NH₂) group by such exemplary groups as acyl (e.g., acetyl or benzoyl), trityl, or substituted trityl (e.g., 4-monomethoxytrityl, 4,4'-dimethoxytrityl). When the amino protecting group is acyl, removal of the acyl group can be accomplished first using catalytic sodium methoxide in methanol or methanolic ammonia, and then the benzyl protecting groups can be removed, for example, by hydrogenolysis, sodium in liquid ammonia, or boron trichloride. When the amino protecting group is trityl or substituted trityl, the trityl or substituted trityl group can be removed first with aqueous acid and the benzyl groups can then be removed.

A compound of formula 1 wherein $R_1$ is

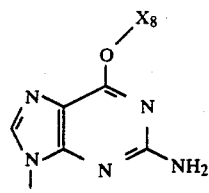

and R$_2$ and R$_3$ are hydrogen can be prepared from a compound of formula 14 or from a compound of formula 1 wherein R$_1$ is

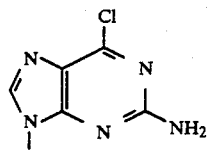

and R$_2$ and R$_3$ are hydrogen by methods known in the art. See, for example, J. F. Gerster, et.al., *J. Amer. Chem. Soc.*, 87, 3752 (1965); K. K. Ogilvie, et.al., *Can. J. Chem.*, 62, 2702 (1984); M. R. Harnden, et.al., *J. Med. Chem.*, 30, 1636 (1987).

Alternatively, this compound of formula 1 can be prepared by reacting a compound of formula

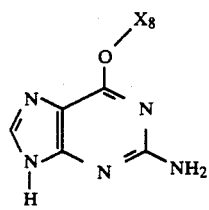

18 with a compound of formula 2 according to the procedures analogous to those used in the preparation of a compound of formula 14, followed by removal of the benzyl protecting groups by methods known in the art. Compounds of formula 18 can be prepared from the compound of formula 13 by methods known in the art (see, e.g., W. A. Bowles et.al., *J. Med. Chem.*, 6, 471 (1963); M. MacCoss, et.al., *Tetrahedron Lett.*, 26, 1815 (1985)).

A compound of formula 1 wherein R$_1$ is

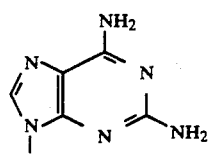

and R$_2$ and R$_3$ are hydrogen can be prepared from a compound of formula 14 by methods known in the art (e.g., J. C. Martin, et.al., *J. Med. Chem.*, 28, 358 (1985)). Thus, for example, when a compound of formula 14 is treated with hot methanolic ammonia, displacement of the chloro group with an amino group will result. Subsequent deprotection of the benzyl protecting groups can be accomplished by hydrogenolysis, by sodium in liquid ammonia, or by using boron trichloride.

Alternatively, this compound of formula 1 can be prepared by reacting an optionally protected compound of formula

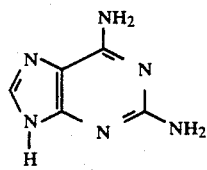

19 with a compound of formula 2 according to the procedures analogous to those used in the preparation of a compound of formula 14, followed by removal of the protecting groups by methods known in the art. The optionally protected forms of compound 19 can be protected at the amino (—NH$_2$) groups by such exemplary groups as acyl, trityl, or substituted trityl.

Reaction of a compound of formula 2 with a compound of formula

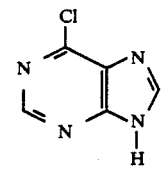

20 by methodology analogous to that used to prepare a compound of formula 14 yields a compound of formula

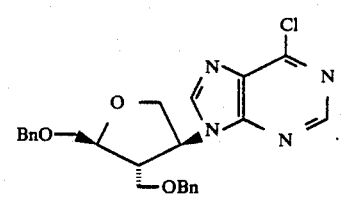

21

Removal of the benzyl protecting groups from a compound of formula 21 yields a compound of formula 1 wherein R$_1$ is

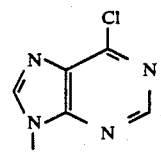

and R$_2$ and R$_3$ are hydrogen. The benzyl protecting groups can be removed by treatment with boron trichloride.

Treatment of a compound of formula 21 with methanolic ammonia and subsequent removal of the benzyl protecting groups, yields the compound of formula 1 wherein R$_1$ is

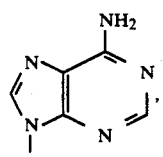

and R$_2$ and R$_3$ are hydrogen.

Alternatively, this compound of formula 1 can be prepared by reaction of a compound of formula 2 with a compound of formula

by methodology analogous to that used to prepare a compound of formula 14 and subsequent removal of the benzyl protecting groups.

Reaction of the compound of formula 2 with a compound of formula

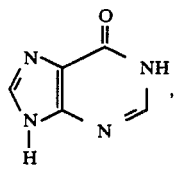

by methodology analogous to that used to prepare a compound of formula 14, and subsequent removal of the benzyl protecting groups yields the compound of formula 1 wherein $R_1$ is

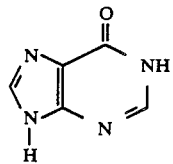

and $R_2$ and $R_3$ are hydrogen.

Alternatively, this compound of formula 1 can be prepared by treatment of the compound of formula 1 wherein $R_1$ is

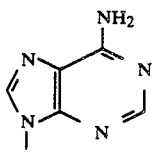

and $R_2$ and $R_3$ are hydrogen with adenosine deaminase or nitrous acid.

Alternatively, this compound of formula 1 can be prepared by subjecting the compound of formula 1 wherein $R_1$ is

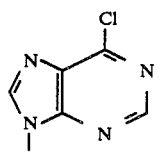

and $R_2$ and $R_3$ are hydrogen to acid hydrolysis (e.g., hot aqueous hydrochloric acid) or basic hydrolysis (e.g., aqueous methanolic sodium hydroxide).

Compounds of formula 1 wherein $R_1$ is

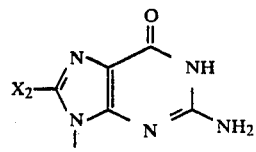

and $X_2$ is methyl, chloro, bromo, iodo, hydroxy, or amino, and $R_2$ and $R_3$ are hydrogen, can be prepared from the corresponding compound of formula 1 wherein $R_1$ is

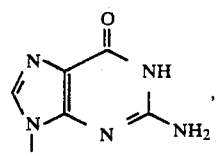

and $R_2$ and $R_3$ are hydrogen by methods known in the art.

The compound of formula 1 wherein $R_1$ is

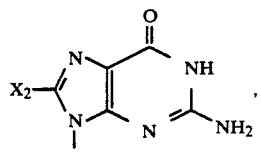

and $X_2$ is fluoro, and $R_2$ and $R_3$ are hydrogen, can be prepared from the corresponding compound of formula 1, wherein $X_2$ is bromo or iodo, and $R_2$ and $R_3$ are hydrogen. The amino (—$NH_2$) and/or hydroxyl groups can be optionally protected with acyl groups. Treatment with fluoride ion (e.g., sodium or potassium fluoride in a solvent such as dimethylformamide or diethylene glycol or tetrabutylammonium fluoride in tetrahydrofuran) followed by removal (if necessary) of the optional acyl protecting groups, using, for example, catalytic sodium methoxide in methanol or methanolic ammonia, provides the compound of formula 1 wherein $R_1$ is

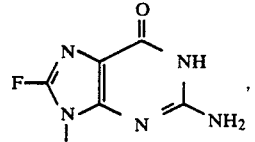

and $R_2$ and $R_3$ are hydrogen.

Compounds of formula 1 wherein $R_1$ is

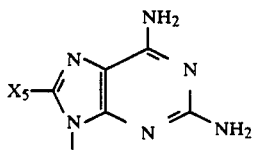

and $X_5$ is methyl, chloro, bromo, iodo, hydroxy, or amino, and $R_2$ and $R_3$ are hydrogen, can be prepared from the corresponding compound of formula 1 wherein $X_5$, $R_2$ and $R_3$ are hydrogen using procedures known in the art. The amino (—NH₂) and/or hydroxyl groups can be optionally protected by acyl groups.

The compound of formula 1 wherein R₁ is

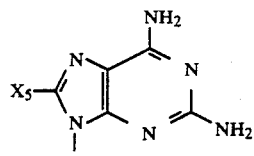

and X₅ is fluoro and R₂ and R₃ are hydrogen can be prepared from the corresponding compound of formula 1 wherein X₅ is bromo or iodo and R₂ and R₃ are hydrogen. The amino (—NH₂) and/or hydroxyl groups can be optionally protected with acyl groups. Treatment with fluoride ion (e.g., sodium or potassium fluoride in a solvent such as dimethyl-formamide or diethylene glycol, or tetrabutyl-ammonium fluoride in tetrahydrofuran) followed by removal (if necessary) of the optional acyl protecting groups, using, for example, catalytic sodium methoxide in methanol or methanolic ammonia, provides the compound of formula 1 wherein R₁ is

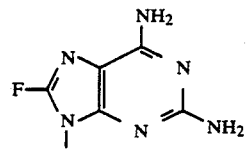

and R₂ and R₃ are hydrogen.

Compounds of formula 1 wherein R₁ is

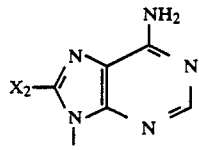

and X₂ is methyl, chloro, bromo, iodo, hydroxy, or amino and R₂ and R₃ are hydrogen can be prepared from the corresponding compound of formula 1 wherein R₁ is

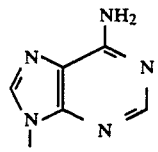

and R₂ and R₃ are hydrogen following procedures known in the art. The amino (—NH₂) and/or hydroxyl groups can be optionally protected by acyl groups.

A compound of formula 1 wherein R₁ is

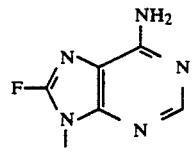

and R₂ and R₃ are hydrogen can be prepared by methodology known in the art from a compound of formula

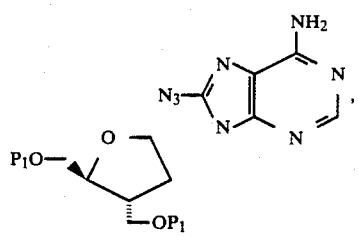

wherein P₁ is an acyl protecting group. A compound of formula 24 can be prepared from a compound of formula 1 wherein R is

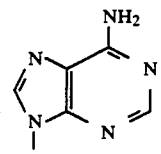

and R₂ and R₃ are hydrogen by methods known in the art.

For general methods of preparing 8-substituted purine nucleosides and nucleoside analogs see, for example: M. J. Robins, et.al., *J. Med. Chem.*, 27, 1486 (1984); R. E. Holmes, et.al., *J. Amer. Chem. Soc.*, 86, 1242 (1964); R.A. Long, et. al., *J. Org. Chem.*, 32, 2751 (1967); R. E. Holmes, et.al., *J. Amer. Chem. Soc.*, 87, 1772 (1965); M. Ikehara, et.al., *Tetrahedron*, 26, 4251 (1970); H. J. Brentnall, et.al., *Tetrahedron Lett.*, 2595 (1972); M. Ikehara, et.al., *Chem. Pharm. Bull.*, 13, 1140 (1965); M. Ikehara, et.al., *Chem. Commun.*, 1509 (1968); E. J. Reist, et.al., *J. Org. Chem.*, 33, 1600 (1968); M. Ikehara, et.al., *Chem. Pharm. Bull.*, 19, 104 (1971).

The compound of formula 1 wherein R₁ is

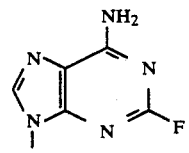

and R₂ and R₃ are hydrogen can be prepared from the corresponding compound of formula 1 wherein R₁ is

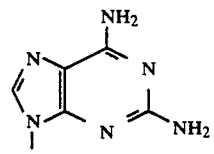

and R₂ and R₃ are hydrogen by following known procedures. See, for example J. A. Montgomery, et. al. in "Synthetic Procedures in Nucleic Acid Chemistry", Vol. 1, W. W. Zorbach and R. S. Tipson, Eds., Interscience Publishers (John Wiley and Sons), N.Y., p. 205, 1968.

The compounds of formula

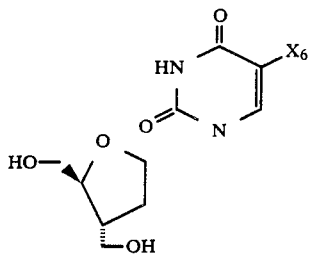

wherein $X_6$ is hydrogen, fluoro, methyl, ethyl, n-propyl, 2-chloroethyl, or 2-fluoroethyl can be prepared by reaction of the corresponding compound of formula

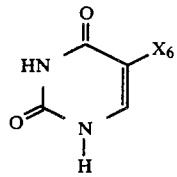

with a compound of formula 2 in the presence of a base such as potassium carbonate, sodium hydride, or potassium hydride, in an aprotic polar solvent (e.g., dimethylformamide, dimethylsulfoxide, or sulfolane), in the optional presence of 18-crown-6 or 15-crown-5, to yield an intermediate of formula

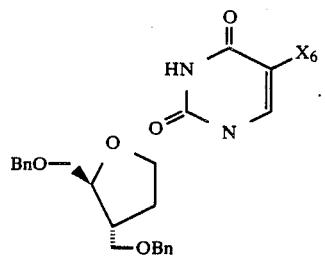

Removal of the benzyl protecting groups provides the corresponding compound of formula 1 wherein $R_1$ is

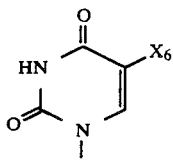

and $R_2$ and $R_3$ are hydrogen. When $X_6$ is hydrogen, fluoro, methyl, ethyl, n-propyl, or 2-fluoroethyl, the benzyl protecting groups can be removed by hydrogenolysis (e.g. palladium hydroxide on carbon in cyclohexene and ethanol; or hydrogen and palladium on carbon, or ammonium formate and palladium black or palladium on carbon, in methanol or ethanol) or by treatment with boron trichloride. When $X_6$ is 2-chloroethyl, the benyzl protecting groups can be removed with boron trichloride.

The compound of formula 26 wherein $X_6$ is 2-chloroethyl or 2-fluoroethyl can be prepared by methods known in the art [H. Griengl, et.al., *J. Med. Chem.*, 30, 1199 (1987); J. Med. Chem., 28, 1679 (1985)].

The compound of formula 25 wherein $X_6$ is fluoro can also be prepared from the corresponding compound 25 wherein $X_6$ is hydrogen and the hydroxy groups are optionally protected with a group such as acyl by fluorination with trifluoromethyl hypofluorite using methodology known in the art. For example, see M. J. Robins, et.al., *J. Amer. Chem. Soc.*, 93, 5277 (1971) and *Chem. Commun.*, 18 (1972); T. S.. Lin, et.al., *J. Med. Chem.*, 26, 1691 (1983).

Compounds of formula 25 wherein $X_6$ is 2-chloroethyl or 2-fluoroethyl can also be prepared from a compound of formula

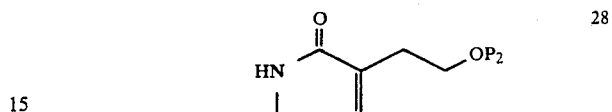

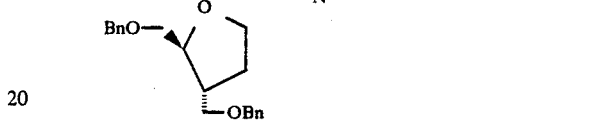

wherein protecting group $P_2$ can be selectively removed in the presence of the benzyl protecting groups. For example, $P_2$ can be a silyl (e.g., t-butyldimethylsilyl, t-butyldiphenylsilyl, (triphenylmethyl)dimethylsilyl, methyldiisopropylsilyl, and triisopropylsilyl), trityl, substituted trityl or acyl group. Selective removal of the protecting group $P_2$ yields a compound having the formula

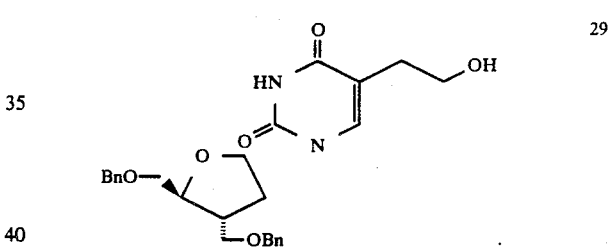

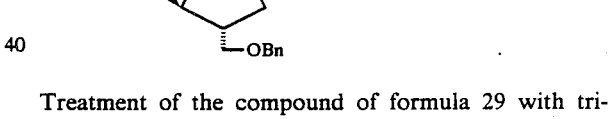

Treatment of the compound of formula 29 with triphenylphosphine-carbon tetrachloride or diethylaminosulfur trifluoride, and subsequent removal of the benzyl protecting groups, affords the compound having the formula 25 wherein $X_6$ is 2-chloroethyl or 2-fluoroethyl, respectively. Alternatively, treatment of a compound 29 with triphenylphos-phine/N-bromosuccinimide or triphenylphosphine/ N-bromosuccinimide/tetrabutylammonium iodide (see H Griengl, et.al., *J. Med. Chem.*, 28, 1679 (1985)) affords compounds having the formula

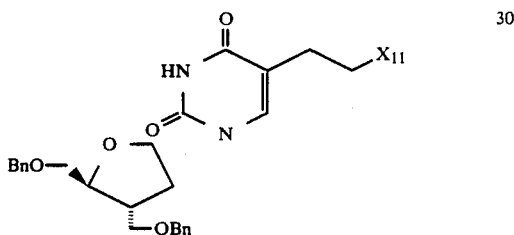

wherein $X_{11}$ is bromo and iodo, respectively. Subsequent treatment with fluoride ion, followed by removal of the benzyl protecting groups, provides the compound of formula 25 wherein $X_6$ is 2-fluoroethyl.

The compounds of formula

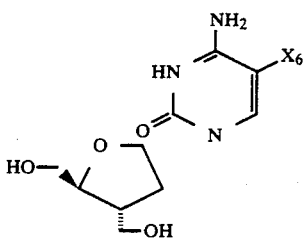

wherein $X_6$ is hydrogen, fluoro, methyl, ethyl, n-propyl, 2-chloroethyl, or 2-fluoroethyl can be prepared from the corresponding compounds of formula 27 by methods known in the art. See for for example, I. Wempner, et.al. in "Synthetic Procedures in Nucleic Acid Chemistry", Vol. 1, W. W. Zorbach and R. S. Tipson, Eds., Interscience Publishers, N.Y., p. 299, 1968; T. S.. Lin, et.al., J. Med. Chem., 26, 1691 (1983); P. Herdewijn, et.al., J. Med. Chem., 28, 550 (1985). When $X_6$ is hydrogen, fluoro, methyl, ethyl, n-propyl, or 2-fluoroethyl, the benzyl protecting groups can be removed by hydrogenolysis (e.g., palladium hydroxide on carbon in cyclohexene and ethanol; or hydrogen and palladium on carbon; or ammonium formate and palladium black or palladium on carbon, in methanol or ethanol) or by treatment with boron trichloride. When $X_6$ is 2-chloroethyl, the benzyl protecting groups can be removed with boron trichloride.

Alternatively, the compound of formula 31 wherein $X_6$ is fluoro, hydrogen, methyl, ethyl, n-propyl, 2-chloroethyl, or 2-fluoroethyl, can be prepared by reaction of the corresponding compound of formula

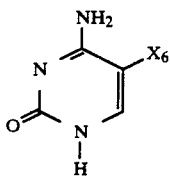

with a compound of formula 2 in the presence of a base such as potassium carbonate, sodium hydride, or potassium hydride in an aprotic solvent (e.g. dimethylformamide, dimethyl sulfoxide, or sulfolane), in the optional presence of 18-crown-6 or 15-crown-5, and subsequent removal of the benzyl protecting groups. Optionally, the amino ($-NH_2$) group in 32 can be protected (e.g., with an acyl group such as acetyl or benzoyl). Removal of this protecting group can be accomplished using sodium methoxide in methanol or methanolic ammonia.

Alternatively, the compound of formula 31 wherein $X_6$ is fluoro can be prepared from the corresponding compound of formula 31 wherein $X_6$ is hydrogen by fluorination with trifluoromethyl hypofluorite using methodology known in the art. Fluorointion can also be performed on the compounds of formula 31 wherein $X_6$ is hydrogen and the hydroxyl and/or amino ($-NH_2$) groups are protected, for example, by an acyl group such as acetyl or benzoyl. After fluorination, deprotection using methanolic ammonia or aqueous hydroxide affords the compound of formula 31 wherein $X_6$ is fluoro. See, for example, M. J. Robbins, et.al., J. Amer. Chem. Soc. 93, 5277 (1971) and Chem. Commun., 18 (1972); T. S. Lin, et.al., J. Med. Chem., 26, 1691 (1983).

The compounds of formula 25 and 31 wherein $X_6$ is chloro, bromo, or iodo can be prepared from the corresponding compounds of formula 25 and 31 wherein $X_6$ is hydrogen by methods known in the art. See, for example, "Basic Principals in Nucleic Acid Chemistry", Vol. 1, P.O.P. Ts'O, Ed., Academic Press, N.Y., P 146, 1974; P. K. Chang in "Nucleic Acid Chemistry" Part 3, L. B. Townsend and R. S. Tipson, Eds., John Wiley and Sons, N.Y., P. 46, 1986.

The compounds of formula 25 and 31 wherein $X_6$ is trifluoromethyl can be prepared from the corresponding compounds of formula 25 and 31 wherein $X_6$ is iodo and the hydroxy groups are protected, for example, by an acyl group, by treatment with trifluoromethyl iodide and copper according to procedures known in the art. Subsequent deprotection using methanolic ammonia or sodium methoxide in methanol yields the corresponding compounds of formulas 25 and 31 wherein $X_6$ is trifluoromethyl. See, for example, Y. Kobayaski, et.al., J. Chem Soc., Perkin 1, 1961 (1983).

The compounds of formula 25 and 31 wherein $X_6$ is

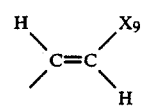

and $X_9$ is chloro, bromo, iodo, hydrogen, methyl or trifluoromethyl can be prepared from the corresponding compounds of formula 25 and 31 wherein $X_6$ is iodo or HgCl via organopalladium intermediates. The compounds of formula 25 and 31 wherein $X_6$ is $-HgCl$ can be prepared from the corresponding compounds of formula 25 and 31 wherein $X_6$ is hydrogen by methods known in the art. See, for example, references in E. De Clercq, et.al., Pharm. Ther., 26, 1 (1984); M. E. Perlman, et.al., J. Med. Chem., 28, 741 (1985); P. Herdewijn, et.al., J. Med. Chem., 28, 550 (1985); D. E. Bergstrom, et.al., J. Med. Chem., 27, 279 (1984)/

Compounds of the formula 1 wherein $R_1$ is

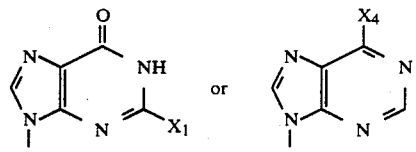

and $X_1$ and $X_4$ are

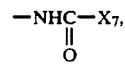

can be prepared from the corresponding compounds of formula 1 wherein $X_1$ and $X_4$ are amino ($-NH_2$) by methods known in the art.

Compounds of formula 1 wherein one or both of $R_2$ and $R_3$ are

can be prepared by methods known in the art from the corresponding compounds of formula 1 wherein $R_2$ and $R_3$ are hydrogen.

For examples of acylation procedures, see "Synthetic Procedures in Nucleic Acid Chemistry", Vol. 1, W. W. Zorbach and R. S. Tipson, Eds., John Wiley and Sons, 1968; "Nucleic Acid Chemistry," Part 1, L. B. Townsend and R. S. Tipson, Eds., John Wiley and Sons, 1978; S. Nishino, et.al., *Nucleosides and Nucleotides*, 5, 159 (1987; A. Matsuda, et.al., *Synthesis*, 385 (1986).

Compounds of the formula 1 wherein $R_1$ is

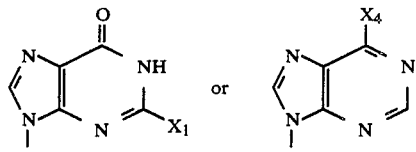

and $X_1$ and $X_4$ are $-N=CHN(X_9)_2$ can be prepared from the corresponding compounds of formula 1 wherein $X_1$ and $X_4$ are amino ($-NH_2$) by procedures known in the art. See, for example, J. Zemlicka and A. Holy, *Collect. Czech. Chem Commun.*, 32, 3159 (1967); K. K. Ogilvie, et.al., Nucleosides and Nucleotides, 4, 507 (1985); L.J. McBride, et.al., J. Amer. Chem. Soc., 108, 2040 (1986).

The compounds of formula 1 wherein $R_2$ and/or Rs are $-PO_2H_2$ can be prepared from the corresponding compounds of formula 1 wherein $R_2$ and $R_3$ are hydrogen by procedures known in the art. See, for example, H. Schaller, et.al., *J. Amer. Chem. Soc.*, 85, 3821 (1963); J. Beres, et.al., *J. Med. Chem.*, 29, 494 (1986); Y. Hayakawa, et.al., *Tetrahedron Lett.*, 28, 2259 (1987); F. Himmelsbach, et.al., *Helv. Chim. Acta.*, 70, 1286 (1987); "Nucleic Acid Chemistry", Part 2, L. B. Townsend and R. S. Tipson, Eds., John Wiley and Sons, 1978.

The compounds of formula 1 wherein $R_1$ is

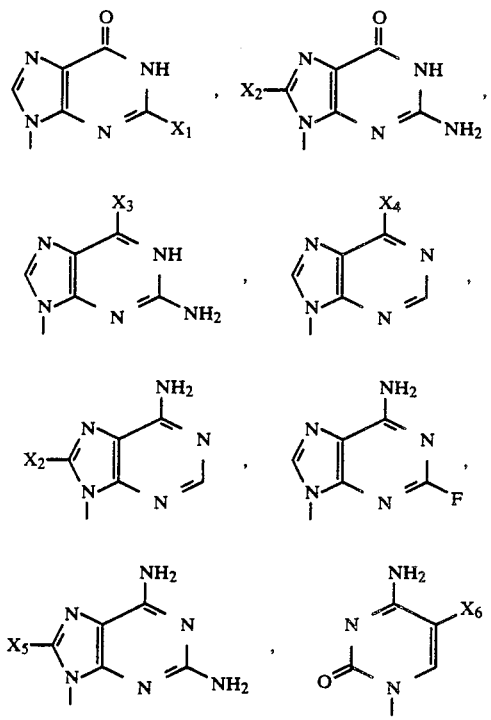

can form acid addition salts with inorganic or organic acids. Illustrative are the hydrohalide (e.g. hydrochloride and hydrobromide), alkyl-sulfonate, sulfate, phosphate and carboxylate salts.

The compounds of formula 1 wherein $R_1$ is

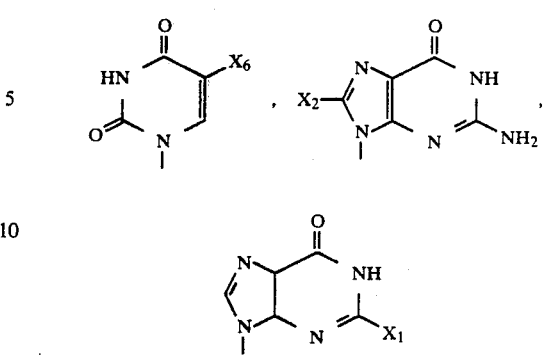

can form basic salts with inorganic and organic bases. Illustrative are alkali metal salts (e.g., sodium and potassium), alkaline earth metal salts (e.g., calcium and magnesium), ammonium and substituted ammonium salts.

The compounds of formula 1 wherein $R_2$ and/or $R_3$ are $-PO_3H_2$ can form basic salts with inorganic and organic bases. Illustrative are alkali metal salts (e.g., sodium and potassium), alkaline earth metal salts (e.g., calcium and magnesium), ammonium and substituted ammonium salts.

The stereochemistry shown for the compounds of this invention is absolute. It is drawn to show that in the compounds of this invention, the absolute stereochemistry is derived from the chiral precursor 1,2-O-(1-methylethylidene)-α-D-xylofuranose.

The following examples are specific embodiments of this invention.

EXAMPLE 1

[3S-(3α,4α,5α)]-2-Amino-1,9-dihydro-9-[tetrahydro-4,5-bis(hydroxymethyl)-3-furanyl ]-6H-purin-6-one.

A. 1,2-O-(1-Methylethylidene)-α-D-xylofuranose, 5-(4-methylbenzenesulfonate)

A solution of 1,2-0-(1-methylethylidene)-a-Dxylofuranose (100 g; 526 mmol) in pyridine (526 ml) was cooled to 0° C. Para-toluenesulfonyl chloride (100 g; 526 mmol) was added as a solution in chloroform (210 ml). The reaction mixture was stirred for 18 hours at room temperature. After this time, 4 ml of water was added and the mixture was stirred for 30 minutes. The reaction mixture was partitioned between water (1.5 L) and chloroform (750 ml). The aqueous layer was extracted with an additional 750 ml of chloroform and the combined organic layers were washed with water (3×1L) and brine (1 L). The organic layer was dried over magnesium sulfate and the volatiles were removed to yield a white solid, which was triturated with ether to afford 132.5 g of the title compound as a white solid. The combined ether triturates were concentrated to dryness and $^1$H NMR analysis of the resulting white solid indicated that it was of equal purity to the first crop of title compound. The two crops were combined to give a total yield of 170.5 g of the title compound.

B. 3,5-Anhydro-1,2-O-(1-methylethylidene)-α-D-xylofuranose 1,2-0-(1-Methylethylidene)-a-D-xylofuranose, 5-(4-methylbenzenesulfonate) (132.5 g, 385 mmol) was stirred in a solution of methanolic sodium methoxide (prepared from 176.6 g of 25% sodium methoxide in methanol diluted with 960 ml of methanol) for 24 hours at room temperature. Water (300 ml) was added and the methanol was removed in vacuo. The resulting aqueous mixture was extracted once with chloroform (1.5 L). The organic layer was washed with water, dried over sodium sulfate and filtered. The filtrate was concentrated to afford the title compound (65.03 g) as a colorless oil.

C.
1,2-O-(1-Methylethylidene)-5-O-(phenylmethyl)-α-D-xylofuranose

Sodium metal (1.32 g, 57.4 mmol) was added at room temperature to benzyl alcohol (51 ml). The mixture was heated at 100° C for 1 hour to afford total dissolution of the metal. The resulting solution was cooled to 80° C and 3,5-anhydro-1,2-O-(1-methylethylidene)-α-D-xylofuranose (4.95 g, 28.7 mmol) was added. The reaction mixture was heated at 100° C. for 18 hours. After cooling to room temperature, the reaction was filtered, and the filtrate was brought to pH 5.5 with acetic acid. The resulting suspension was poured into water and extracted with chloroform (100 ml). The organic layer was washed with water (100 ml), dried over magnesium sulfate, and filtered. The filtrate was concentrated, and the benzyl alcohol was removed by Kuglerohr distillation (50°-60° C., 0.2 mmHg) to afford an orange oil which was crystallized from ether/hexane to afford 4.7 g of the title compound as an off-white solid. The mother liquor was evaportaed and recrystallized from ether/hexane to afford another 2.21 g, giving a total of 6.91 g of the title compound.

Alternatively, sodium metal spheres (34.6 g, 1.5 mol, washed with petroleum ether) were added cautiously in portions to benzyl alcohol (1000 ml) without external cooling. The temperature of the reaction mixture rose to ca. 70° C. The mixture was then heated to 100° C. for 1 to hour to afford total dissolution of the metal. The resulting solution was allowed to cool to 80° C., and a benzyl alcohol (400 ml) solution of 3,5-anhydro-1,2-O-(1-methyl-ethylidene-α-D-xylofuranose (130 g, 0.754 mol) was added. The mixture was heated at 100° C. for 20 hours and then cooled to room temperature. The reaction mixture was partitioned between ether and water, and the organic layer was washed with water until the aqueous layer was neutral. After being washed once with brine, the organic layer was dried over sodium sulfate, filtered, and evaportaed in vacuo. The remaining benzyl alcohol was removed in vacuo at 80° C. to leave a thick, oily residue which was crystallized from ether/pentane (1:1) to give 159 g of the title compound as a white solid.

D.
3-Deoxy-3-methylene-1,2-O-(1-methylethyl-idene)-5-O-(phenylmethyl)-α-D-xylofuranose.

To a rapidly stirred solution of pyridine (110 ml, 1.36 mol) in dichloromethane (1.6 L) at 0° C. under argon was added chromium(VI) oxide (86g, 0.86 mol). After stirring for 30 minutes at room temperature, Celite (220 g) was added and the reaction was placed in a cold water bath. 1,2-O-(1-Methylethylidene)-5-0-(phenylmethyl)-α-D-xylofuranose (30 g, 0.108 mol) in dichloromethane (100 ml) was added rapidly in one portion with rapid stirring. The resulting mixture was stirred for 2 hours at 25° C. and then filtered through a Celite pad. The filter pad was washed well with ether and the combined filtrates were evaporated in vacuo. The resulting residue was triturated with ether and the slurry was filtered through Celite. The filtrate was evaporated in vacuo and the residue was azeotroped twice with toluene and finally triturated again with ether. Filtration through Celite and concentration in vacuo gave crude 1,2-O-(1-methylethylidene)-5-O-(phenylmethyl)-α-D-erythropentofuranos-3-ulose (30.1 g), which was used in the subsequent reaction without further purification.

To a tetrahydrofuran (1.1 L) suspension of methyl triphenylphosphonium bromide (134 g, 0.376 mol) at −7° C. under argon was added n-butyl lithium (210 ml, 0.357 mol, 1.7 M in hexanes). The mixture was warmed to room temperature, resulting in an orange-yellow nearly-homogeneous solution. The reaction mixture was cooled to −70° C. and a tetrahydrofuran (220 ml) solution of 1,2-O(1-methylethylidene)-5-0-(phenylmethyl)-α-D-erythropentofuranos-3-ulose (33.5 g, ca. 0.122 mol, prepared as above) was added. The reaction mixture was stirred at room temperature for 1 hour and then it was heated to 55° C. for 2 hours. The resulting slurry was quenched at 0° C. with saturated ammonium chloride (600 ml) and the aqueous layer was extracted with ethyl acetate three times. The combined organic layers were dried over sodium sulfate and evaporated in vacuo. The oily residue was triturated with 10% ethyl acetate in hexane and filtered. The filtrate was concentrated in vacuo to provide an oil (40 g) which was then purified by flash chromatography (Mallinkrodt SilicAR ®, 100–200 mesh silica gel, type 60A special, 1.1 L), eluting with ethyl acetate:hexanes (5%, then 10%) to give the title compound (26 g) as a colorless oil.

E.
3-Deoxy-3-(hydroxymethyl)-1,2-O-(1-methylethylidene)-5-O-(phenYlmethYl)-α-D-ribo-furanose.

To neat 3-deoxy-3-methylene-1,2-O-(1-methylethylidene)-5-O-(phenylmethyl)-α-D-xylofuranose (16.1 g, 0.058 mol) was added borane-tetrahydrofuran (125 ml, IM solution, 0.125 mol) with rapid stirring. After 1 hour at room temperature, the reaction solution was cooled to 0° C., and tetrahydrofuran/water (60 ml, 1:1), sodium hydroxide (180 ml, 2M), and then 30% hydrogen peroxide (90 ml) were added carefully. The reaction was stirred an additional 65 minutes at room temperature and the volatiles evaporated in vacuo. The residue was partitioned between brine and ethyl acetate and the aqueous layer extracted two more times with ethyl acetate. The combined organic layers were dried over sodium sulfate, filtered, and evaporated. The above residue was combined with one derived from oxidation of 0.012 mol of 3-deoxy-3-methylene-1,2O-(1-methylethylidene)-5-O-(phenylmethyl)-α-D-xylofuranose. The mixture was purified by flash chromatography (Merck silica gel-60, 230 % 400 mesh), eluting with a step-wise gradient of hexanes/ethyl acetate (4:1, 3:1, 7:3, 3:2) to give the title compound (16.4 g) as a colorless solid. $\alpha_D = \times 36°$[c 1.88, CHCl$_3$]; melting point=65.5°-67.0° C.; proton NMR (270 MHz, CDCl$_3$) δ: 7.28-7.25 (m, 5H), 5.81 (d, J=3.5 Hz, 1H), 4.75 (dd, J=3.5, 4.2 Hz, 1H), 4.59 (m, 2H), 4,21 (m, 1H), 3.83 (m, 2H0, 3.65 (m, 2H), 2.70 (nm, 1H), 2.17 (m, 1H), 1.51 (s, 3H), 1.32 (s,3H).

F.
3-Deoxy-1,2-O-(1-methylethylidene)-3-[(phenylmethoxy)methyl]-5-O-(phenyl-methyl)-α-D-ribofuranose.

To a dimethylsulfoxide (150 ml) solution of 3-deoxy-3-(hydroxymethyl)-1,2-O-(1-methylethyli-dene)-5-0-

(phenylmethyl)-α-D-ribofuranose (16.3 g, 0.055 mol) at room temperature was added dimethylsulfoxide sodium salt [31 ml of a 2M solution in dimethylsulfoxide (0.062 mol) generated at 80° C. with sodium hydride]. After 1 hour at room temperature, benzyl bromide (8.6 ml, 0.072 mol) was added dropwise while keeping the reaction vessel in an 18° C. water bath. After 50 minutes at room temperature, a second portion of dimethylsulfoxide sodium salt [10 ml of a 2M solution in dimethylsulfoxide (0.02 mol)] was added, followed 40 minutes later by benzyl bromide (3 ml, 0.012 mol). After a further 1 hour at room temperature, a final portion of dimethylsulfoxide sodium salt [2 ml of a 2M solution in dimethylsulfoxide (4.0 mmol)] was added, followed 30 minutes later by benzyl bromide (0.5 ml, 2.0 mmol). After a further 20 minutes at room temperature, the reaction mixture was stored at −20° C. overnight. The reaction was quenched at 0° C. with saturated ammonium chloride and the aqueous layer extracted three times with ethyl acetate. The combined organic layers were dried over sodium sulfate and the volatiles were evaporated in vacuo. The residue was purified by flash chromatography (Merck silica gel-60, 230–400 mesh), eluting with a stepwise gradient of hexanes/ethyl acetate (9:1, 4:1 and 7:3). This gave the title compound (18.6 g) as a colorless oil.

G.
3-Deoxy-3-[(phenylmethoxy)methyl]-5-O-(phenylmethyl)-D-ribofuranose, diacetate.

A solution of 3-deoxy-1,2-O-(1-methylethyli-dene)-3-[(phenylmethoxy)methyl]-5-0-(phenylmethyl)-α-D-ribofuranose (16.2g, 0.042 mol) in acetic acid/water (3:1 ratio, 450 ml) was heated at 80° C. for 5 hours. The reaction solution was evaporated in vacuo, and the resulting oil was azeotroped twice with toluene and the yellow oily-solid residue used in the subsequent reaction without further purification.

To a pyridine (330 ml) solution of the above residue was added acetic anhydride (50 ml) while keeping the reaction in an 18° C. water bath. The reaction was stirred at room temperature for 7.5 hours, at which time the volatiles were removed in vacuo. The resulting residue was purified by flash chromatography [Merck silica gel-60, 230–400 mesh, eluting with hexanes/ethyl acetate (3:1)]. This purification gave the title compound (16.5 g) as a colorless oil.

H.
1,3-Dideoxy-3-[(phenylmethoxy)methyl]-5-O-(phenylmethyl)-D-ribofuranose.

To a solution of 3-deoxy-3-[(phenylmethoxy)methyl]-5-0-(phenylmethyl)-D-ribofuranose, diacetate (4.81 g, 11.23 mmol) in dichloromethane (100 ml) at 0° C. was added trimethylsilyl bromide (2.59 ml, 19.65 mmol). The reaction was stirred at 0° C. for 30 minutes and at room temperature for 6.5 hours. At this time, the reaction was cooled to 0° C. and transferred via canula to a toluene solution of diisobutylaluminum hydride (100 ml, 1M), also at 0° C. The reaction mixture was kept at 0° C. for 40 minutes and then quenched cautiously with methanol (14.2 ml) and then water (20 ml). After stirring at room temperature for 1 hour, the mixture was filtered through Celite, washing well with ether and ethyl acetate. The volatiles were evaporated in vacuo and the resulting oil (4.04 g) was combined with the crude product (7.6 g) from an identical reaction starting with 23.16 mmol of 3-deoxy-3-[(phenylmethoxy)methyl]-5-0-(phenylmethyl)-D-ribofuranose, diacetate. The combined products were purified by flash chromatography (Merck silica gel-60, 230–400 mesh) eluting with a stepwise dioxane (20:1 and then 7:3). The resulting material was further purified by flash chromatography (Merck silica gel-60, 230–400 mesh) eluting with dichloromethane/dioxane (15:1) to give the title compound as a colorless oil (3.4 g). The mixed fractions were purified by flash chromatography (Merck silica gel-60, 230–400 mesh) eluting with dichloromethane/dioxane (20:1) to give additional title compound as a colorless oil (1.5 g pure and 1.66 g ∼90% pure by ¹H NMR).

Alternatively, a solution of 3-deoxy-3-[(phenylmethoxy)methyl]-5-0-(phenylmethyl)-D-ribofuranose, diacetate (7.85 g, 18.3 mmol) in dry toluene (200 ml) was cooled to 0° C. in an ice bath and treated with a stream of dry hydrogen chloride gas until saturated. The solution was allowed to stand at 0° C. for 20 minutes, and then it was evaporated in vacuo at 25° C. to give an oil. This residue was azeotroped once again with toluene to give crude [3R-(3α,4α,5β)]-2-chlorotetrahydro-4,5bis[(phenylmethoxy)methyl]-3-furanol, acetate, which was used in the subsequent reaction without further purification.

A solution of crude [3R-(3α,4α,5β)]-2-chloro-tetrahydro-4,5-bis[(phenylemthoxy)methyl]-3-fur anol, acetate, (ca. 18.3 mmol, prepared above) in dry toluene (180 ml) was cooled to 0° C. and cannulated with stirring into a 0° C. mixture of diisobutylaluminum hydride (180 ml, 1.0 M solution in toluene) and tetrahydrofuran (180 ml) under nitrogen. The addition took 15 minutes, after which the mixture was stirred for 0.5 hour at 0° C. The mixture was then quenched at 0° C. by dropwise addition of dry methanol (22 ml), followed in 10 minutes by water (32 ml). Ihe mixture was diluted to 1 liter with ether and stirred at room temperature for 1.5 hours. The resulting gel was filtered through Celite and the filter pad washed with ether and ethyl acetate. The filtrates were evaporated in vacuo to an oil, which was taken up in isopropyl ether (10 ml) and diluted with hexane until cloudy. The solution was kept at −30° C. overnight. The resulting crystals were filtered, washed with hexane, and dried in vacuo to give the title compound (4.79 g) as a colorless crystalline solid.

I.
1,3-Dideoxy-3-[(phenylmethoxy)methyl]-5-O-(phenylmethyl)-D-ribofuranose, 2-(4-methylbenzenesulfonate).

1,3-Dideoxy-3-[(phenylmethoxy)methyl]-5-O-(phenylmethyl)-D-ribofuranose (4.71 g, 14.35 mmol) was dissolved in pyridine (28.7 ml) and cooled to 0° C. before adding solid para-toluenesulfonyl chloride (4.38 g, 22.96 mmol). After 1 hour at 0° C., the reaction temperature was increased to 5° C., where it was maintained for 26 hours. Starting material was observed in the reaction after 26 hours, and additional para-toluenesulfonyl chloride (0.078 g, 0.41 mmol) was added. After a total of 70 hours at 5° C., the solvents were removed in vacuo to give an orange residue, which was extracted from saturated sodium bicarbonate solution (200 ml) with ethyl acetate (3×200 ml). The combined organic layers were evaporated in vacuo, and the residue was loaded onto a Merck silica gel-60 (230–400 mesh) column. After elution with hexane/ethyl acetate (3:1) and concentration of the pertinent fractions, the title compound (6.18 g) was isolated as a colorless solid.

J.
[3S-(3α,4α,5β)]-6-(Phenylmethoxy)-9-[tetrahydro-4,5-bis[(phenylmethoxy)methyl]-3-furanyl]-9H-purin-2-amine.

Potassium carbonate (0.3 g, 2.18 mmol) was added to a dimethylformamide (9 ml) suspension of 1,3-dideoxy-3-[(phenylmethoxy)methyl]-5-O-(phenyl-methyl)-D-ribofuranose, 2-(4-methylbenzenesulfonate) (0.557 g, 1.15 mmol), 6-(phenylmethoxy)-9H-purin-2-amine (0.55 g, 2.3 mmol), and 18-crown-6 ether (0.3 g, 1.15 mmol) at room temperature. The mixture was heated to 90° C. for 4 hours and then stirred at room temperature overnight. After a total of 11 hours at 90° C., the solvent was removed by Kugelrohr distillation (40° C., 0.25 mmHg). The orange oily-solid residue was pre-absorbed on silica gel (Baker reagent, 60-230 mesh) and purified by flash chromatography (Merck silica gel-60, 230-400 mesh), eluting with dichloromethane, then a stepwise gradient of isopropyl alcohol/dichloromethane (1, 2, 3, 4, and 8%).

This gave the title compound (0.17 g, corrected for ca. 10% by weight of dimethylformamide) as a colorless powder.

K. [3S-(3α,4β,5α)]-2-Amino-1,9-dihydro-9-[tetrahydro-4,5-bis(hydroxymethyl)-3-fura nyl]-6H-purin-6-one.

To a tetrahydrofuran (3 ml)/ammonia (20 ml) suspension of [3S-(3α,4β,5α)]-6-(phenylmethoxy)-9-[tetrahydro-4,.5-bis[(phenylmethoxy)methyl] -3-furanyl]-9H-purin-2-amine (0.17 g, 0.308 mmol) at −78° C. was added sodium metal (0.3 g, 0.013 mol). The resulting blue solution was stirred at −78° C. for 5 minutes, then allowed to come to reflux, where the blue color disappeared. After cooling to −78° C., additional sodium metal (0.2 g, 0.009 mol) was added, and the reaction warmed to reflux. After a further 20 minutes, the reaction was quenched with solid ammonium chloride and the solvent evaporated with a stream of nitrogen. The resulting white solid was dissolved in water, brought to pH 8 with 0.5N hydrochloric acid, and the solvent evaporated in vacuo. The residue was purified on CHP-20P resin (Mitsubishi Chemical Co., 75-150 μ), eluting first with water, then a continuous gradient of water to 1:1 acetonitrile/water. The fractions containing pure compound were concentrated, and the residue was lyophilized to give the title compound (0.074 g) as a colorless solid. Proton NMR (270 MHz, DMSO-d6) δ: 10.45 (brs, 1H), 7.84 (s, 1H), 6.42 (brs, 2H), 4.93 (m, 1H), 4.86 (m, 1H), 4.78 (m, 1H), 3.45-3.95 (m, 7H), 2.50 (m, 1H); α_D=+6.5° [c 0.29, water/dioxane (5:1)]; M.P.=195-205° C. (dec.).

EXAMPLE 2

[3S-(3α,4β,5α)]-9-[Tetrahydro-4,5-bis(hydroxymethyl)-3-furanyl]-9H-purin-6-amine.

A.
[3S-3α,4β,5α)]-9-[Tetrahydro-4,5-bis-(phenylmethoxy)-methyl]-3-furanyl]-9H-purin -6-amine.

To a dimethylformamide (6 ml) suspension of 1,3-dideoxy-3-[(phenylmethoxy)methyl]-5O-(phenyl-methyl)-D-ribofuranose, 2-(4-methylbenzenesulfonate) (0.335 g, 0.695 mmol), 9H-purin-6-amine (0.28 g, 2.08 mmol), and 18-crown-6 ether (0.18 g, 0.68 mmol) at room temperature was added potassium carbonate (0.37 g, 2.67 mmol). The mixture was heated to 67° C. for 24 hours, then stored at −20° C. overnight. After an additional 9 hours at 90° C., the reaction was cooled to room temperature and the solvent was removed by Kugelrohr distillation (40° C., 0.25 mmHg). The orange oily-solid residue was purified by flash chromatography (Merck silica gel-60, 230-400 mesh) eluting with dichloromethane, then a stepwise gradient of isopropyl alcohol/dichloromethane (2 then 8%). This gave the title compound (0.10 g) as a colorless powder.

B.
[3S-3α,4β,5α)]-9-[Tetrahydro-4,5-bis(hydroxy-methyl)-3-furanyl]-9H-purin-6-amine.

To a tetrahydrofuran (4 ml)/ammonia (25 ml) suspension of [3S-(3α,4β,5α)]-9-[tetrahydro-4,5-bis[(phenylmethoxy)methyl-3-furanyl]-9H-purin-6-amine 0.10 g, 0.225 mmol) at −78° C. was added sodium metal (0.2 g, 8.7 mmol). The resulting blue solution was stirred at −78° C. for 10 minutes, then allowed to come to reflux. After 25 minutes, the reaction was quenched with solid ammonium chloride and the solvent evaporated with a stream of nitrogen. The resulting white solid was re-dissolved in water and neutralized with 0.5N hydrochloric acid, and the solvent evaporated in vacuo. The residue was then purified on CHP-20P resin (Mitsubishi Chemical Co., 75-150 μ), eluting first with water and then a continuous gradient of water to 1:1 acetonitrile/water. The fractions containing desired compound were concentrated and the residue was lyophilized to give the title compound (0.042 g) as a very hydroscopic, slightly yellow solid. Proton NMR (270 MHz, DMSO-d6) δ: 8.25 (s,1H), 8.12 (s, 1H), 7.16 (brs, 2H), 4.99 (m, 1H), 4.94 (t, J=5.3 Hz, 1H), 4.88 (t, J=5.3 Hz, 1H), 3.92-4.00 (m, 2H), 3.53-3.78 (m, 5H), 2.55 (m, 1H); M.P.=185-195° C. (dec.).

EXAMPLE 3

[3S-(3α,4β,5α)]-5-Methyl-1-[tetrahydro-4,5-bis(hydroxymethyl)-3-furanyl]-2,4(1H,3H-pyrimidinedione

A.
[3S-(3α,4β,5α)]-5-Methyl-1-[tetrahydro-4,5-bis[(-phenYlmethoxy)methyl]-3-furanyl]-2,4-(1H,3H)-pyrimidinedione.

1,3-Dideoxy-3-[(phenylmethoxy)methyl]-5O-(phenylmethyl)-D-ribofuranose, 2-(4-methylbenzenesulfonate) sulfonate) (1.20 g, 2.45 mmol), potassium carbonate (1.35 g, 9.8 mmol), 18-crown-6 ether (0.65, 2.45 mmol) and 5-methyl-2,4(1H,3H)-pyrimidinedione (0.62 g, 4.90 mmol) were combined in dry dimethylsulfoxide (14 ml). The reaction was heated to 90° C. for 6.5 hours, then allowed to cool to room temperature. After 48 hours at room temperature, the reaction was centrifuged and the supernatant concentrated in vacuo to a yellow residue. The residue was slurried in dichloromethane, loaded onto a silica gel column (125 ml, Merck silica gel-60, 230-400 mesh) and eluted with ethyl acetate/hexane (7:3, then 1:1) and finally 100% ethyl acetate. The pertinent fractions were combined and concentrated to give the title compound (0.22 g) as a colorless oil.

B.
[3S-(3α,4β,5α)]-5-Methyl-1-[tetrahydro-4,5-bis(hydroxymethyl)-3-furanyl]-2,4-(1H,3H)-pyrimidinedione.

[3S-(3α,4β,5α)]-5-Methyl-1-[tetrahydro-4,5-bis[(-phenylmethoxy)methyl]-3-furanyl]-2,4-(1H,3H)- pyrimidinedione (0.22 g, 0.50 mmol) was combined with palladium hydroxide (0.2 g, 20% on carbon) and cyclohexene (6 ml) in 95% ethanol (20 ml). The reaction was refluxed at 90° C. for 4 hours, then filtered through Celite and washed with methanol/water (1:1). The filtrate was concentrated to a colorless oil in vacuo. The residue was loaded onto a CHP-20P resin (Mitsubishi Chemioal Co., 75–150μ) column and eluted with a continuous gradient of water to 1:1 acetonitrile/water. The pertinent fractions were combined and lyophilized to give the title compound (0.07 g) as a white solid. Proton NMR (270 MHz, DMSO-d6) δ: 11.17 (s, 1H), 7.64 (s, 1H), 4.93 (m, 2H), 4.84 (m, 1H), 3.6–3.9 (m, 7H), 2.23 (m, 1H), 1.75 (s, 3H).

EXAMPLE 4

[3S-3α,4β,5α)]-1-[Tetrahydro-4,5[-bis-(hydroxymethyl)-3-furanyl]-2,4(1H,3H)-pyrimidinedione

A.

[3S-(3α,4β,5α)]-1-[Tetrahydro-4,5-bis-[(phenylmethoxy)methyl]-3-furanyl]-2,4-( 1H,3H)-pyrimidinedione.

1,3-Dideoxy-3-[(phenylmethoxy)methyl]-5O-(phenylmethyl)-D-ribofuranose, 2-(4-methylbenzenesulfonate) (0.94 g, 1.95 mmol), potassium carbonate (1.08 g, 7.80 mmol), 2,4(1H,3H)-pyrimidinedione (0.44 g, 3.90 mmol) and 18-crown-6 ether (0.52 g, 1.95 mmol) were combined in dry dimethylsulfoxide (11 ml). The mixture was heated to 90° C. for 7.5 hours and then cooled to room temperature. The solvent was removed in vacuo to give an orange residue. The residue was loaded onto a silica gel column (Merck silica gel-60, 230–400 mesh) and eluted with ethyl acetate/hexane (3:7, then 1:1) and finally 100% ethyl acetate. The pertinent fractions were combined and concentrated to give the title compound (0.23 g) as a colorless oil.

B.

[3S-(3α,4β,5α)]-1-[Tetrahydro-4,5-bis-(hydroxymethyl)-3-furanyl]-2,4(1H,3 H)-pyrimidinedione.

[3S-(3α, 4β,5α)]-1-[Tetrahydro-4,5-bis-[(phenylmethoxy)methyl]-3-furanyl]-2,4(1 H)-pyrimidinedione (0.22 g, 0.52 mmol) was combined with palladium hydroxide (0.2 g, 20% on carbon) and cyclohexene (6 ml) in 95% ethanol (20 ml). The reaction was refluxed for 6 hours at 90° C. The room temperature solution was then filtered through Celite and the filter cake washed with methanol/water (1:1). Removal of the volatiles in vacuo yielded a colorless oil, which was loaded onto a CHP-20P resin column (Mitsubishi Chemical Co., 75–150μ) and eluted with water, followed by a continuous gradient of water to 1:1 acetonitrile/water. The appropriate fractions were combined, concentrated, and lyophilized to give the title compound (0.075 g) as a white solid. Proton NMR (400 MHz, DMSO-d6) δ: 11.15 (s, 1H), 7.75 (d, J=8.0 Hz, 1H), 5.58 (d, J=8.0 Hz, 1H), 4.80–4.95 (m, 3H), 3.75–3.90 (m, 2H), 3.63–3.72 (m, 2H), 3.50–3.60 (m, 4H), 2.20–2.26 (m, 1H).

EXAMPLE 5

[3S-(3α,4β,5α)]-5-Iodo-1-[tetrahydro-4,5-bis(hydroxymethyl)-3-furanyl]-2,4( 1H,3H)-pyrimidinedione

[3S-(3α,4β,5α)]-1-[Tetrahydro-4,5-bis-(hydroxymethyl)-3-furanyl]-2,4(1H,3H) -pyrimidinedione (0.075 g, 0.31 mmol), iodine (0.09 g, 0.36 mmol) and nitric acid (2.4 ml, 0.8 N) were combined in dioxane (6 ml) and refluxed for 5 hours at 130° C. The solution was cooled to 90° C. before adding solid sodium thiosulfate (0.040 g, 0.25 mmoles), which caused the orange solution to turn yellow. The solvents were removed in vacuo to give a yellow residue which was placed at −20° C. for 48 hours. After the residue was warmed to room temperature, it was slurried in water and loaded onto a CHP-20P resin column (Mitsubishi Chemical Co., 75–150μ). The column was eluted with water, followed by a continuous gradient of water to 1:1 water/acetonitrile. The appropriate fractions were collected, concentrated and lyophilized to give the title compound (0.094 g) as a white solid. Proton NMR (270 MHz, DMSO-d6) δ: 11.56 (s, 1H), 8.26 (s,1H), 4.84–5.20 (m, 3H), 3.4–3.9 (m, 7H), 2.31 (m, 1H); M.P.=90–95° C. (dec.).

EXAMPLE 6

[3S-(3α,4β,5α)]-4-Amino-1-[tetrahydro-4,5-bis(hydroxymethYl)-3-furanyl] TM 2( 1H)-pyrimidinone

A.

[3S-(3α,4β,5α)]-1-[Tetrahydro-4,5-bis-[(phenYlmethoxy)methyl]-3-furanyl]-4-(1H-1,2,4-triazol-1-yl)-2(1H)-pyrimidinone.

[3S-(3α,4β,5α)-1-[Tetrahydro-4,5-bis-[(phenylmethoxy)methyl]-3-furanyl]-2,4(1H, 3H)-pyrimidinedione (0.30 g, 0.72 mmol) was dissolved in dry pyridine (2.37 ml) at 0° C. and para-chlorophenyl phosphodichloridate (0.47 g, 1.92 mmol) was added dropwise, followed by 1,2,4-triazole (0.27 g, 3.91 mmol). The reaction mixture was warmed to room temperature, stirred for 36 hours, and the resulting dark solution was concentrated in vacuo to a brown residue. The residue was dissolved in dichloromethane and washed with water, followed by a saturated sodium bicarbonate solution. The organic layer was concentrated in vacuo to give a purple solid. A 270 ¹H NMR spectrum of the residue indicated a mixture of products. The crude residue was dissolved in dichloromethane, dried over sodium sulfate, filtered and concentrated in vacuo. The resulting residue was azeotroped with pyridine three times and kept under vacuum for 48 hours. This crude residue was dissolved in pyridine (2.37 ml) at 0° C., and p-chlorophenyl phosphodichloridate (0.47 g, 1.92 mmol) was added dropwise, followed by 1,2,4-triazole (0.27 g, 3.91 mmol). After 96 hours at room temperature, the dark solution was concentrated in vacuo to a residue, which was then partitioned between dichloromethane and water. The organic layer was washed with saturated sodium bicarbonate, dried over sodium sulfate, and filtered. Evaporation in vacuo gave the crude title compound (0.68 g) as a brown oil, which was used as is in the next reaction.

B.

[3S-(3α,4β,5α)]-4-Amino-1-[tetrahydro-4,5-bis[(phenylmethoxy)methyl]-3-furanyl ]-2-(1H)-pyrimidinone.

[3S-(3α,4β,5α)]-1-[Tetrahydro-4,5-bis-[(phenylmethoxy)methyl]-3-furanyl]-4-(1H-1,2,4-triazol-1-yl)-2(1H)-pyrimidinone (0.68 g, 1.44 mmol) was slurried in dioxane (9ml) and ammonium hydroxide (3 ml, 29% solution) at room temperature. The reaction mixture was stirred at room temperature for 24 hours and was kept at −20° C. for 4 days. The reaction was concentrated in vacuo to an orange residue, which was dissolved in dichloromethane and washed with 5% sodium hydroxide. The organic layer was dried over sodium sulfate, filtered, and the filtrate concentrated in vacuo to give an oily-residue. The residue was purified by flash chromatography (Merck silica gel-60, 230- 400 mesh), eluting with 4:1 ethyl acetate/isopropyl alcohol. The appropriate fractions were combined and concentrated to give the title compound as an orange residue (0.118 g).

C.

[3S-3α,4β,5α)]-4-Amino-1-[tetrahydro-4,5-bisihydroxymethyl)-3-furanyl]-2(1H)-pyrimidinone.

[3S-(3α,4β,5α)]-4-Amino-1-[tetrahydro-4,5bis-[(phenylmethoxy)methyl]-3-furanyl]-2(1H)-pyrimidinone (0.11 g, 0.26 mmol) was dissolved in 95% ethanol (20 ml) with cyclohexene (6 ml) and palladium hydroxide (20% on carbon, 0.05 g). The mixture was refluxed at 90° C. for 48 hours. After this time, starting material remained (by TLC analysis), and a second portion of palladium hydroxide (20% on carbon, 0.015 g) was added to the reaction. After a further 24 hours at reflux, the reaction was cooled to room temperature and filtered through Celite, washing the filter cake well with 1:1 methanol/water. The filtrate was concentrated in vacuo to give a yellow oil, which was loaded onto a CHP-20P resin column (Mitsubishi Chemical Co., 75–150μ). The column was eluted with water, and the appropriate fractions were combined and lyophilized to give the title compound as an off-white solid (0.048 g). Proton NMR (270 MHz, DMSO-d6) 6: 7.69 (d, J=7.6 Hz, 1H), 7.05 (br s, 2H), 5.70 (d, J=7.0 Hz, 1H), 4.80–5.0 (m, 3H), 3.45–3.85 (m, 7H), 2.05–2.19 (m, 1H).

EXAMPLE 7

3S-(3α(E),4β,5α)]-5-(2-Bromoethenyl)-1-[tetrahydro-4,5-bis(hydroxymethyl)-3-furanyl]-2,4(1H,3H)-pyrimidinedione

A.

[3S-3α,4β,5α)]-1-[Tetrahydro-4,5-bis-(hydroxymethyl)-3-furanyl]-2,4(1H,3H)-pyrimidinedione.

A solution of [3S-(3α,4β,5α)]-1-[tetra-hydro-4,5-bis[(-phenylmethoxy)methyl]-3-furanyl]2,4(1H,3H)-pyrimidinedione (727 mg, 1.72 mmol) in 95% ethanol (66 ml) and cyclohexene (20 ml) was degassed in vacuo, and then 20% palladium hydroxide on carbon (509 mg) was added. The reaction was heated at 90° C. under nitrogen for 3 hours, cooled to room temperature, and filtered through Celite using ethanol (60 ml) to wash the filter pad. Evaporation of the filtrate in vacuo gave a residue, which was dissolved in water (40 ml) and ethyl acetate (30 ml). The separated ethyl acetate layer was extracted with water (20 ml), and the aqueous layers were combined and filtered through a small pad of Celite. Concentration in vacuo gave the desired product as a residue (435 mg), which was used as such in the next reaction.

B.

[3S-(3α,4β,5α)]-5-Iodo-1-[tetrahydro-4,5-bis(hydroxymethyl)-3-furanyl]-2,4(3-furanyl]-2,4-pyrimidinedione.

To a suspension of [3S-(3α,4β,5α)-1-[tetra-hydro-4,5-bis(hydroxymethyl)-3-furanyl]-2,4(1H,3H)-pyrimidinedione (1.72 mmol) in dioxane (35 ml, purified by filtration through basic alumina) was added iodine (874 mg, 3.44 mmol) and 0.8N nitric acid (2.4 ml, 1.92 mmol). The reaction was refluxed under nitrogen for 4 hours, the dark red reaction was cooled to 50° C., and saturated sodium thiosulfate was added until the color was light yellow. The reaction was then concentrated in vacuo, and the residue was slurried in water. Purification on CHP-20P resin (Mitsubishi Chemical Co., 75–150μ),eluting with a continuous gradient of water to 1:1 acetonitrile/water, gave 72 mg of the title compound.

C. [3S-[3α(E),4β,5α]]-3-[1,2,3,4-Tetrahydro-2,4-dioxo-1-[tetrahvdro-4, 5,-bis(hydroxymethyl)-3-furanyl]-5-pvrimidinyl]-2-propenoic acid, methyl ester.

A mixture of palladium (II) acetate (22.8 mg, 0.102 mmol), triphenylphosphine (53 mg, 0.202 mmol) and triethylamine (341 μl 1, 2.4 mmol) in dioxane (24 ml, purified on basic alumina and degassed in vacuo) was heated for 15 minutes at 85° C. under argon. A solution of [3S-(3α,4β,5α)]-5-iodo-1-[tetrahydro-4,5-bis (hydroxymethyl)-3-furanyl]-2,4-(1H,3H)-pyrimidinedione (600 mg, 1.63 mmol) and methyl acrylate (440 μl 4.89 mmol) in dioxane (8 ml, purified on basic alumina and degassed in vacuo) was added, and the reaction was heated at 90° C. for 5 hours. Celite (500 mg) was added, and after stirring at 85° C. for 10 minutes, the slurry was filtered hot through Celite and washed with dioxane (30 ml). The filtrate was concentrated in vacuo to a residue, which was dissolved in methanol and adsorbed onto silica gel. The silica gel was applied to the top of a column of Merck silica gel-60 (150 ml, 230–400 mesh) packed in chloroform. Elution with chloroform followed by chloroform/methanol (20:1 then 10:1) gave 316 mg of desired product containing ca. 28 mol % of triethylammonium salts.

D.

[3S-[3α(E),4β,5α]]-3-[1,2,3,4-Tetrahydro-2,4-dioxo-1-[tetrahydro-4,5bis(hydroxymethyl)-3-furanyl]-5-pyrimidinyl]-2-propenoic acid.

A solution of the above sample (316 mg) of [3S-[3α(E),4α,5β]]-3-[1,2,3,4-tetrahydro-2,4-dioxo-1-[tetrahydro-4,5-bis (hydroxymethyl)-3-furanyl]-5-pyrimidinyl]-2-propenoic acid, methyl ester in 4.84 ml of 2M potassium hydroxide was stirred at room temperature for 1.5 hours. The reaction was cooled to 0° C. and slowly adjusted to pH 2 using 6N hydrochloric acid. The white precipitate was collected by filtration and washed with water (4 ml). Concentration of the filtrate to 2 ml gave a white precipitate, which was collected and washed with water. The combined precipitate was dried in vacuo over P2O5 to give a total of 147 mg of the desired product.

E.

3S-(3α(E),4β,5α)]-5-(2-Bromoethenyl)-1-[tetrahydro-4,5-bis(hydroxymethyl)-3-furanyl]-2,4(1H,3H)-pyrimidinedione To a solution of [3S-[3α(E),4α,5β]]-3-[1,2,3,4-tetrahydro-2,4-dioxo-1-tetrahydro-4,5-bis(hydroxymethyl)-3-furanyl]-5-pyrimidinyl]-2-propenoic acid (143 mg, 0.46 mmol, dried by evaporation of dimethylformamide, 2×4 ml) in dimethylformamide (2 ml) under nitrogen was added potassium bicarbonate (141 mg, 1.41 mmol). A solution of Nbromosuccinimide (84 mg, 0.471 mmol) in dimethylformamide (1 ml) was added, and the reaction was stirred at room temperature for 2.5 hours and filtered (washing with 2 ml of dimethylformamide). Evaporation of the filtrate in vacuo gave a residue, which was concentrated from water (5 ml) twice. The resulting residue was slurried in water (3 ml) and applied to a column of CHP-20P resin (Mitsubishi Chemical Co., 75–150μ) in water. Elution with water and then a continuous gradient of 15% to 40% acetonitrile in water gave, after concentration in vacuo, 89 mg of the title compound. Proton NMR (400 MHz, DMSO-d6) δ: 11.46 (brs, 1H), 8.03 (s,1H), 7.22 (d, J=13.55 Hz, 1H), 6.84 (d, J=13.55 Hz, 1H), 5.03 (m, 1H), 4.94 (m, 1H), 4.83 (m, 1H), 3.4–4.0 (m, 7H), 2.31 (m, 1H); M.P.=142°–143° C.

EXAMPLE 8

[3S-3α,4β,5α)]-4-Amino-5-methyl-1-[tetrahYdro-4,5-bis(hydroxy-methyl)-3-furanyl]-3-furanyl]-2-(1H)-pyrimidinone

A.

[3S-(3α,4β,5α)]-5-Methyl-1-[tetrahydro-4,5-bis[(-phenylmethoxy)methyl]-3-furanyl]-4-(1H-1,2,4-triazoyl-1-yl)-2(1H)-pyrimidinone

[3S-(3α,4β,5α)]-5-Methyl-1-[tetrahydro-4,5-bis[(-phenylmethoxy)methyl-3-furanyl-2,4-1H,3H)-pyrimidinone (410 mg, 0.94 mmol) was dissolved in dry pyridine (3 ml) under argon, cooled to 18° C. in a cool water bath, and p-chlorophenyl phosphodichloridate (413 μl, 623 mg, 2.54 mmol) was added. After the mixture was stirred for 5 minutes, dry 1,2,4-triazole (357 mg, 5.17 mmol) was added, and the reaction mixture was stirred for 4 days at room temperature. The pyridine was removed in vacuo, the reddish-brown glasslike residue was dissolved in dichloromethane (8 ml), and the organic solution was washed with water (2 times 10 ml) and 5% sodium bicarbonate (12 ml), and then dried over anhydrous sodium sulfate. The residue was dried in vacuo overnight at room temperature to give crude [3S-(3α,4β,5α)]-5-methyl-1-[tetrahydro-4,5-bis[(phenylmethoxy)methyl-3 -fura-nyl-4-(1H-1,2,4-triazoyl-1-yl)-2(1H)-pyrimidinone (498 mg), which was used in the next reaction without further purification.

B.

3S-3α,4β,5α)]-4-Amino-5-methyl-1-[tetra-hYdro-4,5-bis[(phenylmethoxy)methyl-3-fura-nyl]-2(1H)-pyrimidinone.

A solution of the above crude [3S-(3α,4β,5α)]-5-methyl-1-[tetrahydro-4,5-bis[(phenylmethoxy) -methyl]-3-furanyl]-4-(1H-1,2,4-triazoyl-1-yl)-2(1H)pyrimidinone (489 mg) in dioxane (10 ml) and concentrated ammonium hydroxide (29% solution, 10 ml) was stirred at room temperature for 24 hours. The volatiles were removed in vacuo yielding a dark oily residue, which was dissolved in dichloromethane (25 ml) and washed with 5% sodium hydroxide. The resulting organic layer was preadsorbed on silica gel (Baker reagent, 60–230 mesh) and purified by flash chromatography (Merck silica gel-60, 230–400 mesh, 125 ml), eluting first with ethyl acetate, then with a gradient of methanol/ethyl acetate (2, 4, 6, and 8%) to give a yellow oil. The yellow oil was redissolved in dichloromethane and evaporated in vacuo to give the title compound (276 mg) as a yellow solid.

C. [3S-(3α, 4β,5α])]-4-Amino-5-methyl-1-[tetra-hydro-4,5-bis(hydroxymethyl)-3-furanyl]-2(1H)-pyrimidinone.

A solution of [3S-(3α,4β,5α)]-4-amino-5-methyl-1-[tetrahydro-4,5-bis[(phenylmethoxy)methyl ]-3-furanyl-2(1H)-pyrimidinone (273 mg, 0.63 mmol) in 95% ethanol (40 ml) and cyclohexene (20 ml) was refluxed at 90° C. with palladium hydroxide (20% on carbon, 136 mg) under an argon atmosphere. After heating for 26 hours, the hot reaction mixture was filtered through a Celite pad, washing the filter pad with a mixture of methanol:water (1:1). The volatiles were removed in vacuo, and the residue was dissolved in water (5 ml) and purified on a CHP-20P resin column (Mitsubishi Chemical Co., 75–150 μ, 30 ml), eluting first with water, then with 5% acetonitrile/water. The appropriate fractions were combined, the volatiles were removed in vacuo, and the residue was slurried in water and lyophilized to give the title compound (127 mg) as a colorless solid. Proton NMR (270 MHz, DMSO-d6) 8.01 (brs, 2H), 7.84 (s, 1H), 4.94 (m, 2H), 4.85 (brs, 2H), 3.60–3.90 (m, 4H), 3.55 (m, 3H), 2.25 (m, 1H), 1.90 (s, 3H); M.P.=208°–212° C. (dec.).

EXAMPLE 9

[3S-(3α,4β,5α)]-4-Amino-5-iodo-1-[tetrahydro-4,5-bis(-hydroxymethyl)-3-furanyl]-pyrimidinone To a solution of [3S-(3α,4β,5α)]-4-amino-1-[tetrahydro-4,5-bis(hydroxymethyl)-3furanyl]in water (160 ml), acetic acid (320 μl) and carbon 5 tetrachloride (80 μl) was added iodic acid (36 mg, 0.204 mmol) and iodine (60 mg, 0.236 mmol). The resulting mixutre was heated at 50° C. for 2 hours and it was then concentrated in vacuo to yield a dark residue. The excess iodine was removed from the residue by azeotroping several times with methanol. The crude material was dissolved in water (3 ml), and the pH was adjusted to 7 with 1 N sodium hydroxide. The aqueous mixture was purified on a CHP-20P resin column (Mitsubishi Chemical Co., 75–150 μ, 20 ml) eluting with water (150 ml) and then 5% acetonitrile/water (300 ml). The appropriate fractions were combined, the volatiles were removed in vacuo, and the residue dissolved in water and lyophilized to give the title compound (55 mg) as a colorless solid. Proton NMR (270 MHz, DMSO-d6) δ: 8.16 (s, 1H), 7.65 (brs, 1H), 6.50 (brs, 1H), 4.92 (t, J=5.2 Hz, 1H), 4.87 (m, 1H), 4.80 (t, J=5.2 Hz, 1H), 3.60–3.90 (m, 4H), 3.51 (m, 3H), 2.24 (m, 1H); M.P.=212–216° C. (dec.).

EXAMPLE 10

Treatment of Viral Infection in Cell Culture in Vitro

Assays were performed in cell culture systems to determine the concentrations of compounds that are effective in preventing several kinds of viral infections. The assays and results are described below.

Abbreviations:

HSV-1 (herpes simplex virus type 1), HSV-2 (herpes simplex virus type 2), VZV (vari-cella-zoster virus), HCMV (human cytomegalovirus), VV (vaccinia virus).

Cell Culture Assays:

HSV-1, HSV-2, HCMV, VZV, and VV antiviral assays: Virus was adsorbed to WI-38 cell culture monolayers in 6 well culture plates (Costar, Cambridge, MA) for 1 hour prior to addition of maintenance medium containing duplicate dilutions of the test compound. Inhibition of plaque development was evaluated on fixed and stained monolayers after 4 days incubation at 37° C. for HSV-1, HSV-2, and VV and after 5–7 days incubation at 37° C. for HCMV and VZV. ID50 values were determined from the drug concentration which conferred at least a 50% plaque reduction compared to virus controls (See Table 1).

TABLE 1
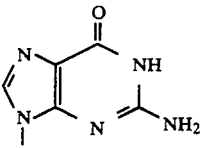
| $R_1$ | ID$_{50}$ ($\mu$M) for the following viruses | | | | | |
|---|---|---|---|---|---|---|
| | HSV-1 (strain schooler) | HSV-2 (strain 186) | VZV (strain Ellen) | VZV (strain Oka) | HCMV (strain AD169) | VV (strain CL) |
| 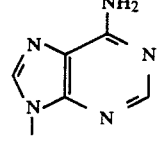 | 7 | 1.8 | 18–36 | ND* | 356 | >356 |
| 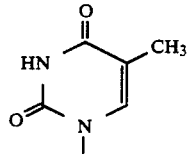 | 3.8–7.5 | 3.8–7.5 | 1.9–3.8 | ND | 1.9–3.8 | 8–19 |
| 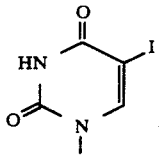 | 2–4 | 195–390 | 8–19 | ND | >390 | ND |
| 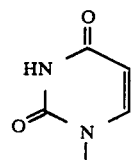 | 68–136 | >272 | 27–68 | ND* | >272 | ND |
| 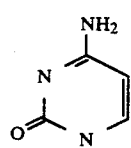 | >413 | >413 | 41–103 | ND | >413 | ND |
| 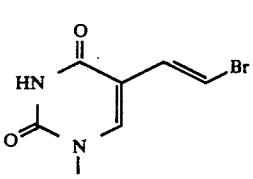 | 21–41 | 21–41 | 0.2–0.4 | ND | 41–104 | 41–415 |
|  | 1.4–2.8 | >288 | >288 | 1.4 | >288 | ND* |

TABLE 1-continued

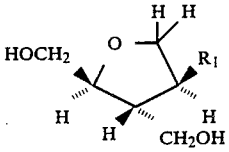

| | ID$_{50}$ ($\mu$M) for the following viruses | | | | | |
|---|---|---|---|---|---|---|
| R$_1$ | HSV-1 (strain schooler) | HSV-2 (strain 186) | VZV (strain Ellen) | VZV (strain Oka) | HCMV (strain AD169) | VV (strain CL) |
| 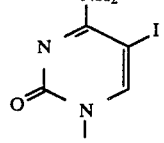 | 68–136 | >272 | 5–14 | ND | >272 | ND |
| 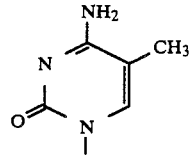 | 392 | 392 | 40 | ND | >392 | ND |

*ND = not determined

What is claimed is:
1. A compound having the formula

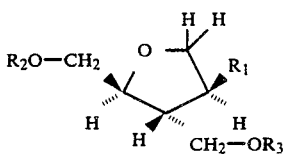

and pharmaceutically acceptable salts thereof wherein R$_1$ is

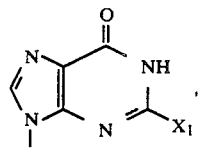 , 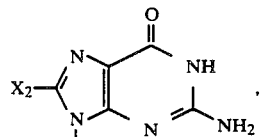 ,

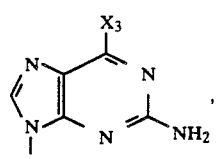

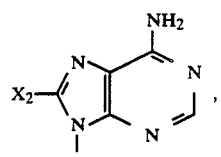 , 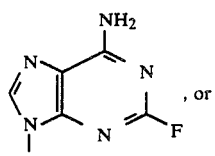 , or

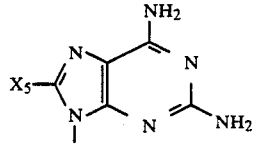

wherein X$_1$ is hydrogen, amino,

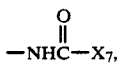

—N=CHN(X$_8$)$_2$
X$_2$ is methyl, fluoro, chloro, bromo, iodo, hydroxy, or amino,
X$_3$ is hydrogen, chloro, or O-X$_8$,
X$_4$ is amino, chloro,

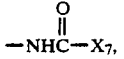

or —N=CHN(X$_8$)$_2$
X$_5$ is hydrogen, methyl, fluoro, chloro, bromo, iodo, hydroxy, or amino,
R$_2$ and R$_3$ are independently hydrogen, —PO$_3$H$_2$, or

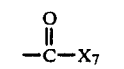

the term "alkyl" refers to straight and branched chained groups of 1 to 10 carbons,
the term "substituted alkyl" refers to alkyl groups having one or more substituents selected from the group consisting of halogen, amino, axiod, hydroxy, cyano, trialkylammonium (wherein each alkyl group has 1 to 6 carbons), alkoxy of 1 to 6 carbons, phenyl, substituted phenyl, and carboxy, and the term "substituted phenyl" refers to a phenyl substituted with one, two, or three groups selected from the group consisting of alkyl of 1 to 6 carbons, alkoxy of 1 to 6 carbons, halogen, trifluoromethyl, amino, alkylamino of 1 to 6 carbons, halogen, trifluoromethyl, amino, alkylamino of 1 to 6 carbons, dialkylamino (wherein each alkyl group has 1 to 6 carbons), nitro, cyano, alkanoyloxy of 2 to 11 carbons, carboxy, carbonyl, and hydroxy.

2. A compound in accordance with claim 1 wherein R₂ and R₃ are independently hydrogen or

3. A compound in accordance with claim 1 wherein R₂ and R₃ are independently hydrogen or —PO₃H₂.

4. A compound in accordance with claim 1 wherein R₂ and R₃ are hydrogen.

5. A compound in accordance with claim 1 wherein R₁ is

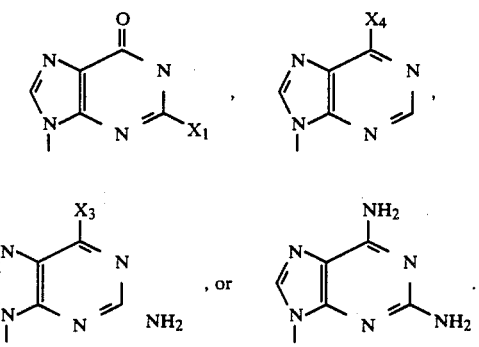

6. A compound in accordance with claim 5 wherein R₁ is

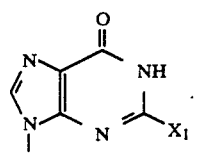

7. A compound in accordance with claim 5 wherein R₁ is

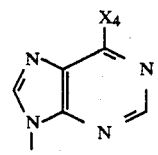

8. A compound in accordance with claim 5 wherein R₁ is

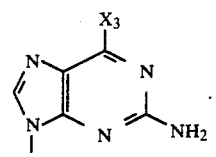

9. A compound in accordance with claim 5 wherein R₁ is

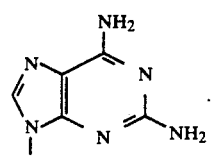

10. A compound in accordance with claim 6 wherein R₁ is

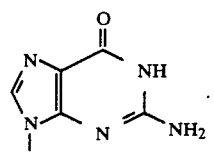

11. A compound in accordance with claim 7 wherein R₁ is

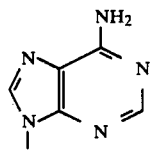

12. A compound in accordance with claim 1, [3S-(3α,4β,5α)]-2-Amino-1,9-dihydro-9-[tetrahydro-4,5-bis(hydroxymethyl)-3-furanyl]-6H-purin-6-one.

13. A compound in accordance with claim 1, [3S-(3α,4β,5α)]-9-[Tetrahydro-4,5-bis(hydroxymethyl)-3-furanyl]-9H-purin-6-amine.

* * * * *

UNITED STATES PATENT AND TRADEMARK OFFICE
CERTIFICATE OF CORRECTION

PATENT NO. : 5,059,690
DATED : October 22, 1991
INVENTOR(S) : Robert Zahler and Joseph A. Tino It is certified that error appears in the above-identified patent and that said Letters Patent is hereby corrected as shown below:

Title page, [22] Filed - date is listed as May 1, 1990.

Correct date is March 1, 1990.

Signed and Sealed this

Twenty-fourth Day of January, 1995

Attest:

Attesting Officer

BRUCE LEHMAN

Commissioner of Patents and Trademarks